(12) United States Patent
Winqvist et al.

(10) Patent No.: US 11,434,258 B2
(45) Date of Patent: Sep. 6, 2022

(54) COMPOUNDS (IMMUNORHELINS)

(71) Applicant: ISR IMMUNE SYSTEM REGULATION HOLDING AB (PUBL), Stockholm (SE)

(72) Inventors: Ola Winqvist, Uppsala (SE); Emma Lindh, Knivsta (SE); Robert Wallin, Bålsta (SE); Matt Gregory, Cambridge (GB); Steven Moss, Cambridge (GB)

(73) Assignee: ISR IMMUNE SYSTEM REGULATION HOLDING AB, Stockholm (SE)

( * ) Notice: Subject to any disclaimer, the term of this patent is extended or adjusted under 35 U.S.C. 154(b) by 175 days.

(21) Appl. No.: 16/479,507

(22) PCT Filed: Jan. 19, 2018

(86) PCT No.: PCT/EP2018/051345
§ 371 (c)(1),
(2) Date: Jul. 19, 2019

(87) PCT Pub. No.: WO2018/134370
PCT Pub. Date: Jul. 26, 2018

(65) Prior Publication Data
US 2019/0389908 A1    Dec. 26, 2019

(30) Foreign Application Priority Data

Jan. 20, 2017 (EP) .................. 17152456

(51) Int. Cl.
C07K 7/23    (2006.01)
A61K 38/00   (2006.01)

(52) U.S. Cl.
CPC ............ *C07K 7/23* (2013.01); *A61K 38/00* (2013.01)

(58) Field of Classification Search
None
See application file for complete search history.

(56) References Cited

U.S. PATENT DOCUMENTS

| | | |
|---|---|---|
| 7,834,141 B1 | 11/2010 | Siler-Khodr |
| 8,349,805 B2 | 1/2013 | Bevec et al. |
| 9,388,216 B2 | 7/2016 | Millar et al. |
| 2004/0152369 A1 | 8/2004 | Siler-Khodr |
| 2004/0235748 A1 | 11/2004 | Igari |
| 2004/0259803 A1 | 12/2004 | Boyd |
| 2005/0043245 A1 | 2/2005 | Siler-Khodr |
| 2012/0045393 A1 | 2/2012 | Linder |

FOREIGN PATENT DOCUMENTS

| | | |
|---|---|---|
| EP | 1382350 A1 | 1/2004 |
| GB | 2237571 A | 5/1991 |
| JP | 2003-012552 A | 1/2003 |
| JP | 2004-512011 A | 4/2004 |
| JP | 2007-518699 A | 7/2007 |
| JP | 2009-539952 A | 11/2009 |
| JP | 2010-539008 A | 12/2010 |
| WO | 200174377 A1 | 10/2001 |
| WO | 200230435 A1 | 4/2002 |
| WO | 2003051272 A2 | 6/2003 |
| WO | WO 2004/094599 A2 | 11/2004 |
| WO | 2007144554 A2 | 12/2007 |
| WO | 2009033663 A1 | 3/2009 |
| WO | WO 2009/033701 A1 | 3/2009 |
| WO | 20090145690 A1 | 12/2009 |
| WO | 2018134372 A1 | 7/2018 |

OTHER PUBLICATIONS

Limonta et al. ("GnRH receptors in cancer": From cell biology to novel targeted therapeutic strategies; Endocrine Reviews, Oct. 2012, 33(5):784-811).*
cancer.gov (accessed Sep. 24, 2021).*
International Search Report of the International Searching Authority for Application No. PCT/EP2018/051345, dated Mar. 15, 2018, 4 pages.
Written Opinion of the International Searching Authority for Application No. PCT/EP2018/051345, dated Mar. 15, 2018, 6 pages.
International Preliminary Report on Patentability for PCT/EP2018/051345, dated Mar. 27, 2019, 8 pages.
Doron, Bacterial infections: Overview; International Encyclopedia of Public Health, 2008:273-282.
Garcia-Gomez, Role of Sex Steroid Hormones in Bacterial-Host Interactions; Hindawi 2013 vol. 2013, Article ID 928290 (11 pages).
Millar et al., 1989 "Chimeric Analogues of Vertebrate Gonadotropin-releasing Hormones Comprising Substitutions of the Variant Amino Acids in Positions 5, 7, and 8. Characterization of requirements for receptor binding and gonadotropin release in mammalian and avian pituitary gonadotropes," J Biol Chem 264(35):21007-13.
ITH/ISR Immune System Regulation: "An open phase II study in HIV-1 infected untreated male adult patients to evaluate safety and tolerability and the in vivo effects on T cell population and viral load of a GnRH analogue administered by intranasal administration during 28 days when combined with a single intramuscular testosterone depot injection to restore a normal serum testosterone level", Apr. 30, 2014 (Apr. 30, 2014), pp. 1-13, XP055394073.
Saussez et al., 2014 "Towards neuroimmunotherapy for cancer: the neurotransmitters glutamate, dopamine and GnRH-II augment substantially the ability of T cells of few head and neck cancer patients to perform spontaneous migration, chemotactic migration and migration towards the autologous tumor, and also elevate markedly the expression of CD3zeta and CD3epsilon TCR-associated chains," J Neural Transm (Vienna) 121(8):1007-27.
CDC (https://www.cdc.gov/fungal/diseases/index.htrnl accessed May 21, 2021) (2 pages).

(Continued)

Primary Examiner — Julie Ha
Assistant Examiner — Tara L Martinez
(74) Attorney, Agent, or Firm — Glenn Foulds; Carl A. Morales; Fenwick & West LLP

(57) ABSTRACT

The present invention provides immune stimulating peptides (immunorhelins) capable of stimulating GnRH receptors when dosed to human patients or cells. These immunorhelins have utility in treating viral diseases and cancer.

12 Claims, 4 Drawing Sheets

Figure 1:
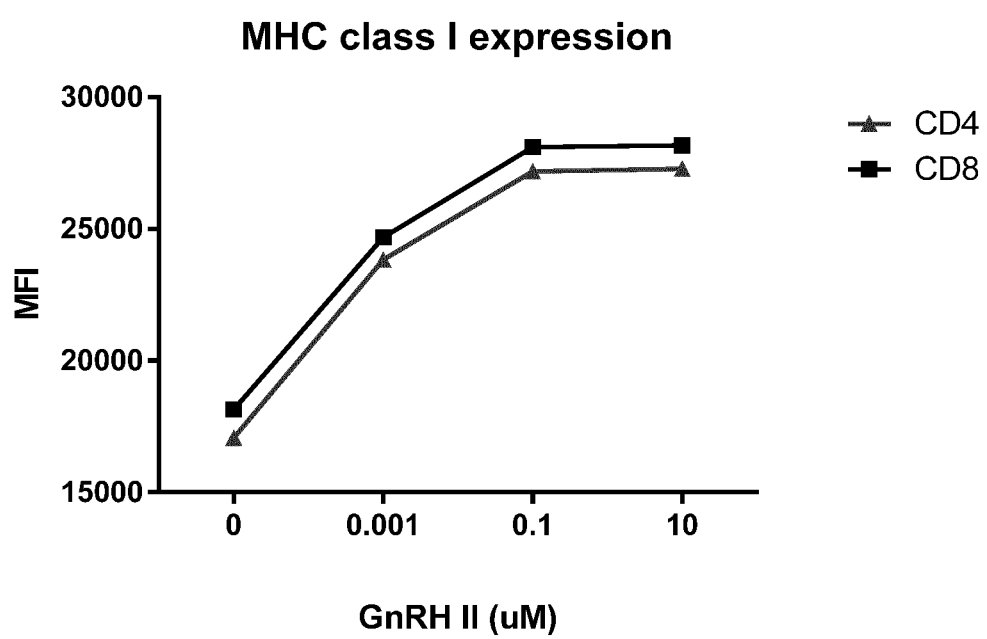

Specification includes a Sequence Listing.

(56) References Cited

OTHER PUBLICATIONS

National Institute of Health (https://www.niaid.nih.gov/research/antimicrobial-resistance-threats Feb. 11, 2020) (3 pages).
Kamaruzzaman, N. et al., "Targeting the hard to reach: challenges and novel strategies in the treatment of intracellular bacterial infections," *British Journal of Pharmacology*, vol. 174, Issue 14, 2016, pp. 2225-2236.
Arver, S. et al., "Serum dihydrotestosterone and testosterone concentrations in human immunodeficiency virus-infected men with and without weight loss," *Journal of Andrology*, vol. 20, Issue 5, Sep.-Oct. 1999, pp. 611-618.
Bardsley, V. et al., "Massive lymphocytic infiltration of uterine leiomyomas associated with GnRH agonist treatment," *Histopathology*, Jul. 1998; 33(1):80-2.
Brockmeyer, G. et al., "Prevalence of endocrine dysfunction in HIV-infected men," *Hormone Research*, 2000; 54(5-6):294-5.
Eidne, K.A. et al., "Gonadotropin-releasing hormone (GnRH)-binding sites in human breast cancer cell lines and inhibitory effects of GnRH antagonists," *The Journal of Clinical Endocrinology & Metabolism*, vol. 64, Issue 3, Mar. 1, 1987, pp. 425-432, https://doi.org/10.1210/jcem-64-3-425.
Illing et al., "Comparative Sequence Analysis and Functional Characterization of the Cloned Sheep Gonadotropin-releasing Hormone Receptor Reveal Differences in Primary Structure and Ligand Specificity among Mammalian Receptors," *Biochemical and Biophysical Research Communications*, 1993, 196(2), 745-51, 2 pages.
immunopaedia.org, "Internet archive of 4. MHC & Antigen Presentation," Dec. 8, 2016, Retrieved from internet on Nov. 18, 2021, https://web.archive.org/web/20161208044034/https://www.immunopaedia.org.za/immunology/basics/4-mhc-antigen-presentation/, 8 pages.
Iseda and Matano, "Progress toward prevention and cure of HIV infection" with abridged English translation, AIDS Research Center, National Institute of Infectious Diseases, vol. 33, No. 17, 2015, pp. 2727-2731.
Jacobson, J.D. and Ansari, M.A., "Immunomodulatory actions of gonadal steroids may be mediated by gonadotropin-releasing hormone," *Endocrinology*, vol. 145, Issue 1, Jan. 1, 2004, pp. 330-336, https://doi.org/10.1210/en.2003-0510.
Jacobson, J.D. et al., "Gonadotropin-releasing hormone increases CD4-T-lymphocyte numbers in an animal model of immunodeficiency," *Journal of Allergy and Clinical Immunology*, vol. 104, Issue 3, Sep. 1999, pp. 653-658.
Kerr-Layton, J.A. et al., "Chronic plasma cell endometritis in hysterectomy specimens of HIV-infected women: a retrospective analysis," Infectious Diseases in Obstetrics and Gynecology, 1998; 6(4):186-90.
Mcclean, G. and Mccluggage, W.G., Unusual morphologic features of uterine leiomyomas treated with gonadotropin-releasing hormone agonists: massive lymphoid infiltration and vasculitis, International Journal of Surgical Pathology, Oct. 2003, vol. 11, issue 4, pp. 339-344.
Morgan et al., "A transcriptionally active human type II gonadotropin-releasing hormone receptor gene homolog overlaps two genes in the antisense orientation on chromosome 1q.12," *Endocrinology*, vol. 144, Issue 2, Feb. 1, 2003, pp. 423-436, https://doi.org/10.1210/en.2002-220622.
White, R.B. et al., "Second gene for gonadotropin-releasing hormone in humans," PNAS, Jan. 6, 1998, vol. 95, pp. 305-309; https://doi.org/10.1073/pnas.95.1.305.

\* cited by examiner

```
                          SEQUENCE LISTING

<160> NUMBER OF SEQ ID NOS: 95

<210> SEQ ID NO 1
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 1

Glu His Trp Ser His Ser Leu Arg Pro Gly
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 2

Glu His Trp Ser Tyr Ser Trp Arg Pro Gly
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 3

Glu His Trp Ser Tyr Ser Leu Tyr Pro Gly
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 4

Glu His Trp Ser His Ser Trp Arg Pro Gly
```

```
1               5                    10
```

<210> SEQ ID NO 5
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 5

```
Glu His Trp Ser His Ser Leu Tyr Pro Gly
1               5                    10
```

<210> SEQ ID NO 6
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 6

```
Glu His Trp Ser His Ser Leu Arg Pro
1               5
```

<210> SEQ ID NO 7
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 7

```
Glu His Trp Ser Tyr Ser Trp Tyr Pro Gly
1               5                    10
```

<210> SEQ ID NO 8
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 8

```
Glu His Trp Ser Tyr Ser Trp Arg Pro
1               5
```

<210> SEQ ID NO 9
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 9

```
Glu His Trp Ser Tyr Ser Leu Tyr Pro
1               5
```

<210> SEQ ID NO 10
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 10

```
Glu His Trp Ser His Ser Trp Arg Pro
1               5
```

<210> SEQ ID NO 11
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 11

Glu His Trp Ser His Ser Leu Tyr Pro
1               5

<210> SEQ ID NO 12
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 12

Glu His Trp Ser Tyr Ser Trp Tyr Pro
1               5

<210> SEQ ID NO 13
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 13

Glu His Trp Ser His Ser Trp Tyr Pro
1               5

<210> SEQ ID NO 14
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 14

Glu His Trp Ser Tyr Trp Leu Tyr Pro Gly
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 15

Glu His Trp Ser Tyr Trp Leu Arg Pro
1               5

<210> SEQ ID NO 16
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 16

Glu His Trp Ser His Trp Leu Tyr Pro Gly
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 17

Glu His Trp Ser His Trp Leu Arg Pro
1               5

<210> SEQ ID NO 18
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 18

Glu His Trp Ser Tyr Trp Trp Arg Pro
1               5

<210> SEQ ID NO 19
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 19

Glu His Trp Ser Tyr Trp Leu Tyr Pro
1               5

<210> SEQ ID NO 20
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 20

Glu His Trp Ser His Trp Trp Arg Pro
1               5

<210> SEQ ID NO 21
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 21

Glu His Trp Ser His Trp Leu Tyr Pro
1               5

<210> SEQ ID NO 22
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 22

Glu His Trp Ser Tyr Trp Trp Tyr Pro
1               5

```
<210> SEQ ID NO 23
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 23

Glu His Trp Ser His Phe Leu Arg Pro Gly
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 24

Glu His Trp Ser Tyr Phe Trp Arg Pro Gly
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 25

Glu His Trp Ser Tyr Phe Leu Tyr Pro Gly
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 26

Glu His Trp Ser Tyr Phe Leu Arg Pro
1               5

<210> SEQ ID NO 27
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 27

Glu His Trp Ser His Phe Trp Arg Pro Gly
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 28

Glu His Trp Ser His Phe Leu Tyr Pro Gly
1               5                   10

<210> SEQ ID NO 29
```

```
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 29

Glu His Trp Ser His Phe Leu Arg Pro
1               5

<210> SEQ ID NO 30
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 30

Glu His Trp Ser Tyr Phe Trp Tyr Pro Gly
1               5                   10

<210> SEQ ID NO 31
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 31

Glu His Trp Ser Tyr Phe Trp Arg Pro
1               5

<210> SEQ ID NO 32
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 32

Glu His Trp Ser Tyr Phe Leu Tyr Pro
1               5

<210> SEQ ID NO 33
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 33

Glu His Trp Ser His Phe Trp Tyr Pro Gly
1               5                   10

<210> SEQ ID NO 34
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 34

Glu His Trp Ser His Phe Trp Arg Pro
1               5

<210> SEQ ID NO 35
<211> LENGTH: 9
```

```
<212> TYPE: PRT
<213> ORGANISM: Artificial Sequence
<220> FEATURE:
<223> OTHER INFORMATION: Man-made analogue of GnRH II

<400> SEQUENCE: 35

Glu His Trp Ser His Phe Leu Tyr Pro
1               5

<210> SEQ ID NO 36
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 36

Glu His Trp Ser Tyr Phe Trp Tyr Pro
1               5

<210> SEQ ID NO 37
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 37

Glu His Trp Ser His Leu Leu Arg Pro Gly
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 38

Glu His Trp Ser Tyr Leu Trp Arg Pro Gly
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 39

Glu His Trp Ser Tyr Leu Leu Tyr Pro Gly
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 40

Glu His Trp Ser His Leu Trp Arg Pro Gly
1               5                   10

<210> SEQ ID NO 41
<211> LENGTH: 10
<212> TYPE: PRT
```

```
<213> ORGANISM: Artificial Sequence
<220> FEATURE:
<223> OTHER INFORMATION: Man-made analogue of GnRH II

<400> SEQUENCE: 41

Glu His Trp Ser His Leu Leu Tyr Pro Gly
1               5                   10

<210> SEQ ID NO 42
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 42

Glu His Trp Ser His Leu Leu Arg Pro
1               5

<210> SEQ ID NO 43
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 43

Glu His Trp Ser Tyr Leu Trp Tyr Pro Gly
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 44

Glu His Trp Ser Tyr Leu Trp Arg Pro
1               5

<210> SEQ ID NO 45
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 45

Glu His Trp Ser Tyr Leu Leu Tyr Pro
1               5

<210> SEQ ID NO 46
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 46

Glu His Trp Ser His Leu Trp Tyr Pro Gly
1               5                   10

<210> SEQ ID NO 47
<211> LENGTH: 9
<212> TYPE: PRT
<213> ORGANISM: Artificial Sequence
```

```
<220> FEATURE:
<223> OTHER INFORMATION: Man-made analogue of GnRH II

<400> SEQUENCE: 47

Glu His Trp Ser His Leu Trp Arg Pro
1               5

<210> SEQ ID NO 48
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 48

Glu His Trp Ser His Leu Leu Tyr Pro
1               5

<210> SEQ ID NO 49
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 49

Glu His Trp Ser Tyr Leu Trp Tyr Pro
1               5

<210> SEQ ID NO 50
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 50

Glu His Trp Ser His Leu Trp Tyr Pro
1               5

<210> SEQ ID NO 51
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 51

Glu His Trp Ser His His Leu Arg Pro Gly
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 52

Glu His Trp Ser Tyr His Trp Arg Pro Gly
1               5                   10

<210> SEQ ID NO 53
<211> LENGTH: 10
<212> TYPE: PRT
<213> ORGANISM: Artificial Sequence
<220> FEATURE:
```

<223> OTHER INFORMATION: Man-made analogue of GnRH II

<400> SEQUENCE: 53

Glu His Trp Ser Tyr His Leu Tyr Pro Gly
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 54

Glu His Trp Ser His His Trp Arg Pro Gly
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 55

Glu His Trp Ser His His Leu Tyr Pro Gly
1               5                   10

<210> SEQ ID NO 56
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 56

Glu His Trp Ser His His Leu Arg Pro
1               5

<210> SEQ ID NO 57
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 57

Glu His Trp Ser Tyr His Trp Arg Pro Gly
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 58

Glu His Trp Ser Tyr His Trp Arg Pro Gly
1               5                   10

<210> SEQ ID NO 59
<211> LENGTH: 9
<212> TYPE: PRT
<213> ORGANISM: Artificial Sequence
<220> FEATURE:
<223> OTHER INFORMATION: Man-made analogue of GnRH II

```
<400> SEQUENCE: 59

Glu His Trp Ser Tyr His Leu Tyr Pro
1               5

<210> SEQ ID NO 60
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 60

Glu His Trp Ser His His Trp Arg Pro
1               5

<210> SEQ ID NO 61
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 61

Glu His Trp Ser His His Leu Tyr Pro
1               5

<210> SEQ ID NO 62
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 62

Glu His Trp Ser Tyr His Trp Tyr Pro
1               5

<210> SEQ ID NO 63
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 63

Glu His Trp Ser His His Trp Tyr Pro
1               5

<210> SEQ ID NO 64
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 64

Glu His Trp Ser His Ser Trp Tyr Pro Gly
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Man-made analogue of GnRH II
```

```
<400> SEQUENCE: 65

Glu His Trp Ser His Trp Leu Arg Pro Gly
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 66

Glu His Trp Ser Tyr Trp Trp Arg Pro Gly
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 67

Glu His Trp Ser His Trp Trp Arg Pro Gly
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 68

Glu His Trp Ser Tyr Trp Trp Tyr Pro Gly
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 69

Glu His Trp Ser His Trp Trp Tyr Pro Gly
1               5                   10

<210> SEQ ID NO 70
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 70

Glu His Trp Ser His Trp Trp Tyr Pro
1               5

<210> SEQ ID NO 71
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 71
```

```
Glu His Trp Ser His Phe Trp Tyr Pro
1               5

<210> SEQ ID NO 72
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 72

Glu His Trp Ser His Leu Trp Tyr Pro Gly
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 73

Glu His Trp Ser Tyr Trp Leu Arg Pro Gly
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 74

Glu His Trp Ser Tyr Phe Leu Arg Pro Gly
1               5                   10

<210> SEQ ID NO 75
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 75

Glu His Trp Ser Tyr Ser Leu Arg Pro
1               5

<210> SEQ ID NO 76
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 76

Glu His Trp Ser Tyr His Leu Arg Pro
1               5

<210> SEQ ID NO 77
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 77
```

```
Glu His Trp Ser Tyr Leu Leu Arg Pro
1               5
```

<210> SEQ ID NO 78
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 78

```
Glu His Trp Ser Tyr Ser Leu Arg Pro
1               5
```

<210> SEQ ID NO 79
<211> LENGTH: 10
<212> TYPE: PRT
<213> ORGANISM: Homo sapiens
<220> FEATURE:
<223> OTHER INFORMATION: GnRH I

<400> SEQUENCE: 79

```
Glu His Trp Ser Tyr Gly Leu Arg Pro Gly
1               5                   10
```

<210> SEQ ID NO 80
<211> LENGTH: 10
<212> TYPE: PRT
<213> ORGANISM: Homo sapiens
<220> FEATURE:
<223> OTHER INFORMATION: GnRH II

<400> SEQUENCE: 80

```
Glu His Trp Ser His Gly Trp Tyr Pro Gly
1               5                   10
```

<210> SEQ ID NO 81
<211> LENGTH: 20
<212> TYPE: DNA
<213> ORGANISM: Homo sapiens
<220> FEATURE:
<223> OTHER INFORMATION: Type I GnRH Receptor forward primer

<400> SEQUENCE: 81
tgcctcttca tcatccctct                                              20

<210> SEQ ID NO 82
<211> LENGTH: 20
<212> TYPE: DNA
<213> ORGANISM: Homo sapiens
<220> FEATURE:
<223> OTHER INFORMATION: Type I GnRH Receptor reverse primer

<400> SEQUENCE: 82
gcaaatgcaa ccgtcatttt                                              20

<210> SEQ ID NO 83
<211> LENGTH: 20
<212> TYPE: DNA
<213> ORGANISM: Homo sapiens
<220> FEATURE:
<223> OTHER INFORMATION: Type II GnRH Receptor forward primer

<400> SEQUENCE: 83
actgttcaat ggctggctgt                                              20

<210> SEQ ID NO 84
<211> LENGTH: 20
<212> TYPE: DNA
<213> ORGANISM: Homo sapiens
<220> FEATURE:
<223> OTHER INFORMATION: Type II GnRH Receptor reverse primer

<400> SEQUENCE: 84
gcccccagaa gtttccttac                                              20

<210> SEQ ID NO 85
<211> LENGTH: 10
<212> TYPE: PRT
<213> ORGANISM: Artificial Sequence
<220> FEATURE:
<223> OTHER INFORMATION: Man-made anallogue of GnRH II

<400> SEQUENCE: 85

Glu His Trp Ser Tyr Trp Trp Tyr Pro Gly
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 86

Glu His Trp Ser Tyr Trp Trp Arg Pro Gly
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 87

Glu His Trp Ser His Trp Trp Tyr Pro Gly
1               5                   10

<210> SEQ ID NO 88
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 88

Glu His Trp Ser Tyr His Trp Arg Pro
1               5

<210> SEQ ID NO 89
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 89

Glu His Trp Ser His Trp Leu Arg Pro Gly
1               5                   10

<210> SEQ ID NO 90
<211> LENGTH: 10

```
<212> TYPE: PRT
<213> ORGANISM: Artificial Sequence
<220> FEATURE:
<223> OTHER INFORMATION: Man-made analogue of GnRH II

<400> SEQUENCE: 90

Glu His Trp Ser His Leu Trp Tyr Pro Gly
1               5                   10

<210> SEQ ID NO 91
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 91

Glu His Trp Ser His Leu Trp Tyr Pro
1               5

<210> SEQ ID NO 92
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 92

Glu His Trp Ser His Ser Trp Tyr Pro Gly
1               5                   10

<210> SEQ ID NO 93
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 93

Glu His Trp Ser His Ser Trp Tyr Pro
1               5

<210> SEQ ID NO 94
<211> LENGTH: 10
<212> TYPE: PRT
<213> ORGANISM: Artificial Sequence
<220> FEATURE:
<223> OTHER INFORMATION: Man-made analogue of GnRH II

<400> SEQUENCE: 94

Glu His Trp Ser His Trp Trp Tyr Pro Gly
1               5                   10

<210> SEQ ID NO 95
<211> LENGTH: 9
<212> TYPE: PRT
<213> ORGANISM: Artificial Sequence
<220> FEATURE:
<223> OTHER INFORMATION: Man-made analogue of GnRH II

<400> SEQUENCE: 95

Glu His Trp Ser His Trp Trp Tyr Pro
1               5
```

COMPOUNDS (IMMUNORHELINS)

FIELD OF THE INVENTION

The present invention provides a set of novel peptides capable of stimulating the immune system, named immunorhelins. The invention also provides novel peptides capable of stimulating GnRH receptors on leukocytes. The present invention relates to novel compounds as such and to the compounds for use in medicine, notably in the treatment of viral diseases such as HIV, and the immunotherapeutic treatment of cancer. The immunorhelins may also be used as immunomodulating adjuvants in vaccination. The novel GnRH receptor stimulating immunorhelins maximizes the modulating effects of the immune system while minimizing the therapeutically unwanted endocrine effects. The present invention also provides methods for preparing immunorhelins of the invention that have improved properties for use in medicine.

BACKGROUND OF THE INVENTION

CD4$^+$ T cells are key mediators of the immune response and are primary targets for infection of HIV. Existing antiretroviral therapy for HIV is compromised by patient compliance, drug toxicity and drug resistance. Thus there is a great need in the art for methods and means of increasing the immune competence of CD4$^+$ T cells in HIV and in several immunologically related viral diseases as well as in cancer.

GnRH I (also known as gonadotropin releasing hormone or LHRH), is a decapeptide with the structure pyroGlu-His-Trp-Ser-Tyr-Gly-Leu-Arg-Pro-Gly-NH$_2$. It is produced as a 92 amino-acid propeptide which is modified post-translationally to form the final peptide with pyroglutamic acid at the amino terminus and a carboxamide at the carboxyl terminus. It has long been known that it is responsible for release of FSH and LH from the anterior pituitary gland, and is normally released from the hypothalamus in a pulsative manner. Suraphysiological levels of GnRH I induce an immediate increase of FSH and LH secretion, soon followed by inhibition of FSH and LH secretion. This is due to the fact that high levels of GnRH I have an inhibitory effect on the GnRH I receptors of the anterior pituary gland. Continuous administration of GnRH I at high unphysiological levels thus induces pharmacological castration (1). A large number of GnRH I agonists and antagonists have been synthesized for use in therapeutic areas such as hormone sensitive cancer. Initially, salts of GnRH I were used therapeutically (such as gonadorelin hydrochloride and gonadorelin diacetate tetrahydrate). Further drug discovery and development led to the clinical use of a wide variety of agents, including buserelin, triptorelin, nafarelin, histrelin and leuprorelin, each of which has improvements over gonadorelin such as extended half-life and super-agonism of the GnRH I receptor.

It has been reported that GnRH I not only exhibits hormonal effects but also may stimulate the immune system (2). McClean and McCluggage (3) observed massive infiltration of small mature lymphocytes in uterine leiomyomas after preoperative treatment with a GnRH I receptor agonist. Bardsley et al (4) made the same observation, indicating a stimulatory effect on migration of GnRH I on the immune cells. Reports have been made on chronic plasma cell endometritis in hysterectomy specimens from HIV-infected women in a retrospective analysis (5), and on elevated levels of FSH and LH (hypergonadotropic) in HIV-infected men (6-7). By administering GnRH I to diabetes-prone BB rats exhibiting an AIDS-like lymphocyte profile the CD4 T-lymphocyte numbers was increased (8).

INTRODUCTION TO THE INVENTION

In humans, two variants of GnRH peptide exist, GnRH I and GnRH II, coded for by different genes. The structure of GnRH II is pyroGlu-His-Trp-Ser-<u>His</u>-Gly-<u>Trp</u>-<u>Tyr</u>-Pro-Gly-NH$_2$ (differences from GnRH I underlined). GnRH II is a nonhypothalamic form primarily produced outside the brain, and has been suggested to be involved in the non-endocrine aspects of the GnRH system (9). Surprisingly, we found an effect of GnRH II stimulation on the MHC class I expression on T cells demonstrating that GnRH II directly activates these cells (FIG. 1).

Figure 4:
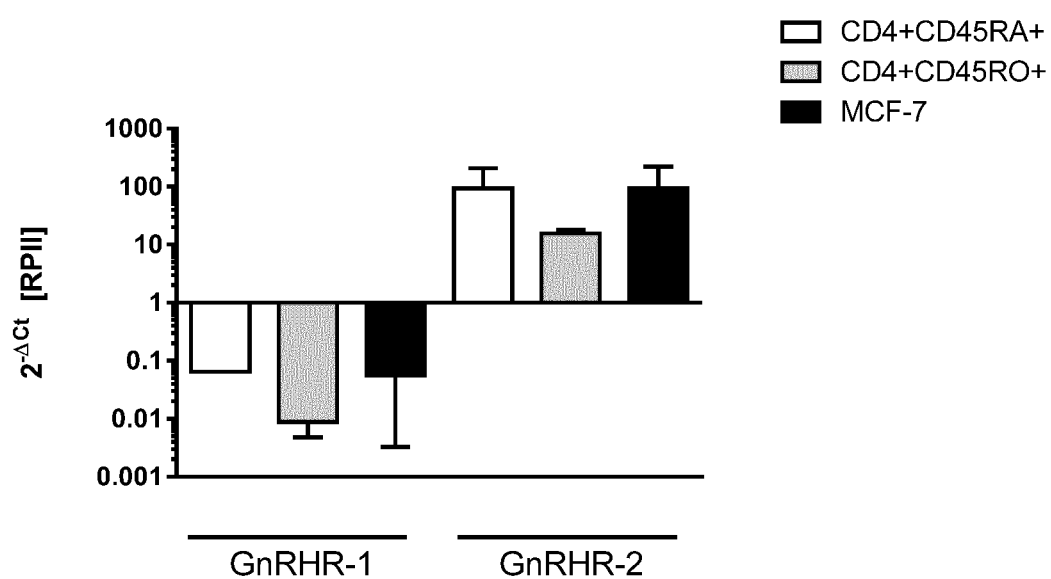

Unlike other mammals, only one conventional human GnRH receptor has been described, the type I GnRH receptor. The type II GnRH receptor homologue is present on chromosome 1q12 gene in humans but contains a frame shift and a stop codon and is believed not to be functionally expressed (10). Surprisingly, our findings suggest that the type II GnRH receptor is indeed expressed on T cells as they respond to GnRH stimulation by increased MHC class I expression (FIG. 1). These functional findings were substantiated by qPCR analysis where we could demonstrate expression of the type II GnRH receptor mRNA. In addition, the relative expression level of the type II GnRH receptor was higher compared to the expression levels of the type I GnRH receptor on naive and memory T cells (FIG. 4). Thus, we have identified that the expression of the type II GnRH receptor is the dominant receptor expressed on T cells, functionally responsive to GnRH stimulus.

We have also discovered that GnRH I analogs may activate T cells leading to MHC class I expression. In a recent clinical trial using the GnRH I analog Buserelin as treatment for HIV, HIV infected men were provided with sex hormone substitution to minimize the endocrine effects of GnRH I. These effects are mediated by GnRH I binding to pituitary type I GnRH receptors, causing decreased testosterone production and subsequently impotence. It is very likely that GnRH I in addition to its endocrine effects cross-signal and stimulate the immune system by binding to the type II GnRH receptor on T cells when high castrating levels of GnRH analogues are used. Interestingly, GnRH I binding to receptors expressed in breast cancer cells displays a low binding affinity (Kd, 1.6-3.0×10(−6) M), whereas central pituitary binding of GnRH I displays a 1000-fold higher affinity (Kd, 4.8×10(−9) M) (11).

It is likely that the difference in binding affinity of GnRH I and GnRH II peptides reflects the expression of type I GnRH receptors specialised for GnRH I binding on pituitary cells, whereas peripheral cells may have dominated expression of type II GnRH receptor and therefore low affinity and an "off target" effect of GnRH I binding. Thus, our unexpected finding that the type II GnRH receptor is the dominating receptor on T cells is novel and may explain the receptor physiology of GnRH I and GnRH II. Therefore, by using GnRH II-like peptides in the treatment of HIV the endocrine effect should be minimized and the immune stimulation effect isolated and enhanced.

Based on these discoveries, the inventors have made human GnRH II-like peptides, termed immunorhelins, in order to optimise immune stimulating effects and minimize the effect on the hormonal system. These immunorhelins have use in stimulating MHC class I capable of leading to an immune response clearing infectious agents, such as HIV and in treating cancer. Therefore, several GnRH II-like peptides are disclosed which have potent binding to GnRH II receptors but preferably weaker binding to GnRH I receptors, leading to a comparable or stronger MHC class I response, but a weaker 'off-target' effect on hormone stimulation or inhibition.

DESCRIPTION OF THE INVENTION

In one aspect, the present invention provides peptide-based analogues of human GnRH II.

Thus, in one aspect of the invention there is provided a peptide of Formula (I):

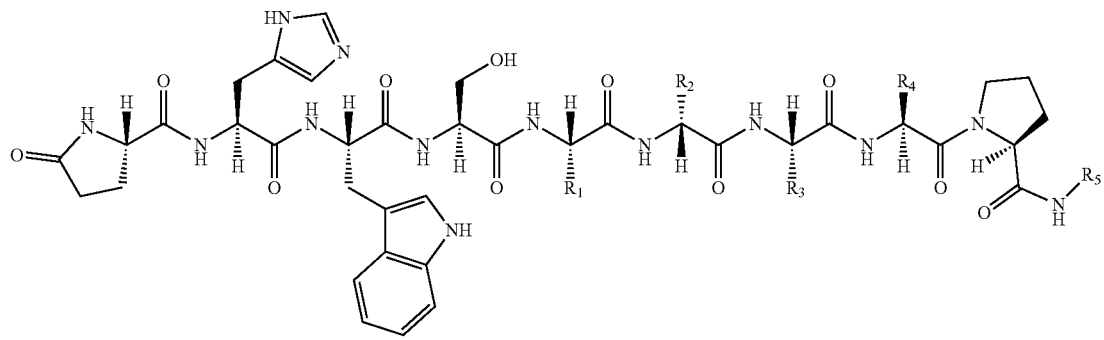

(I)

or a pharmaceutically acceptable salt thereof, and wherein

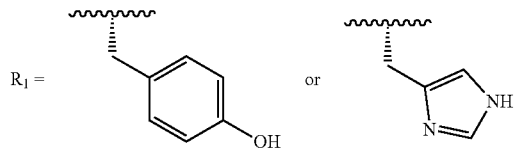

$R_2 =$
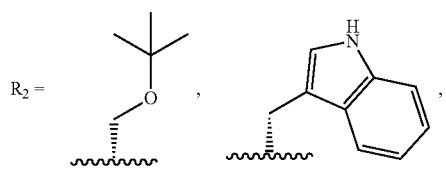

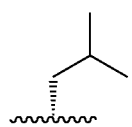

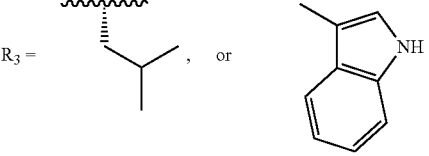

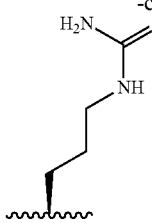

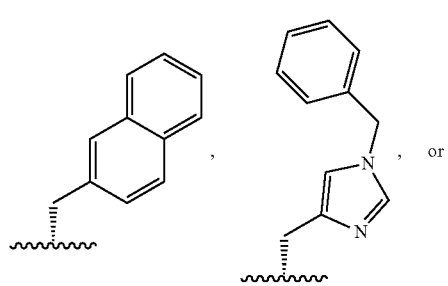

$R_5$=Me, Et, $CH_2CF_3$, iPr, nPr, nBu, iBu, sBu, tBu, cyclopropyl, $CH_2CONH_2$, or $NHCONH_2$ Formula I regarding the compounds of the invention can also be expressed as:

pGlu-His-Trp-Ser-$AA_1$-$AA_2$-$AA_3$-$AA_4$-Pro-X, wherein:

$AA_1$ is selected from His and Tyr $AA_2$ is selected from D-Ser(OtBu), D-Trp, D-NaI, D-Bhi, and D-Leu $AA_3$ is selected from Leu and Trp $AA_4$ is selected from Arg and Tyr X is selected from —NHMe, —NHEt, —NHCH$_2$CF$_3$, —NHiPr, —NHnPr, —NHnBu, —NHiBu, —NHsBu, —NHtBu, —NHcyclopropyl, —NH—NH—CONH$_2$ and —NHCH$_2$CONH$_2$ The invention does not include the following compounds of formula (I):

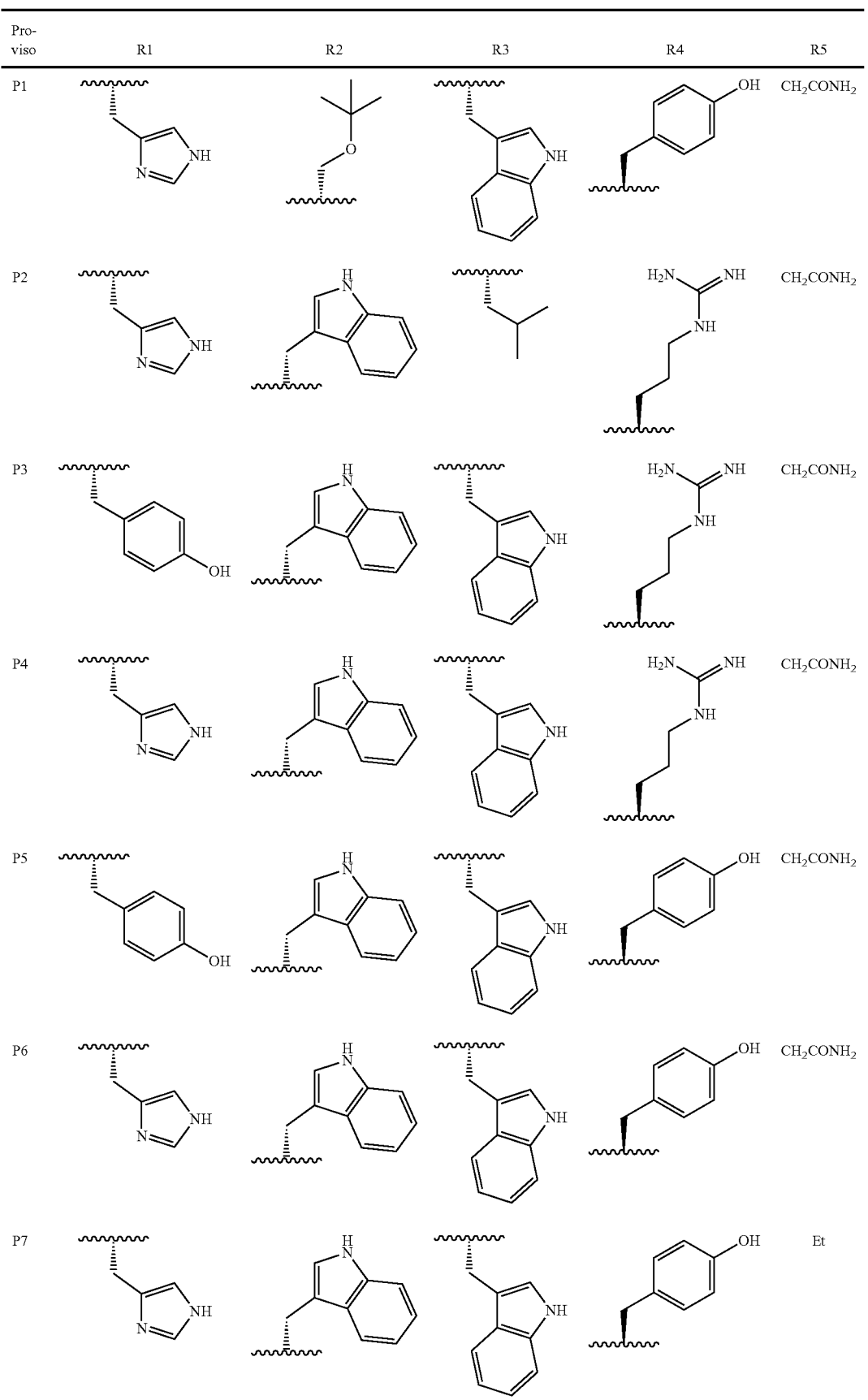

-continued
| Proviso | R1 | R2 | R3 | R4 | R5 |
|---|---|---|---|---|---|
| P8 | 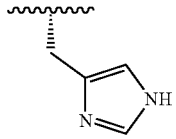 | 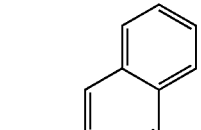 | 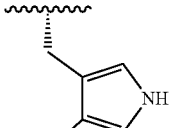 | 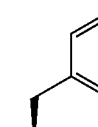 | Et |
| P9 | 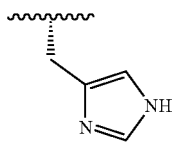 | 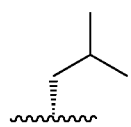 | 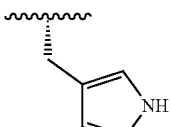 | 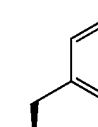 | $CH_2CONH_2$ |
| P10 | 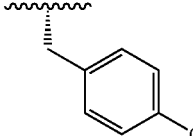 | 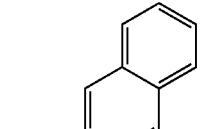 | 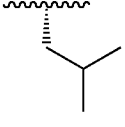 | 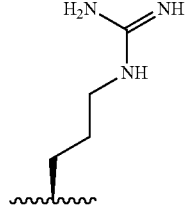 | $CH_2CONH_2$ |
| P11 | 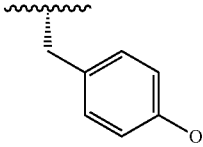 | 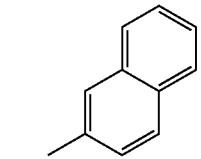 | 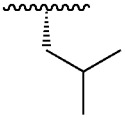 | 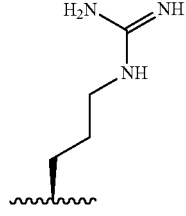 | $CH_2CONH_2$ |
| P12 | 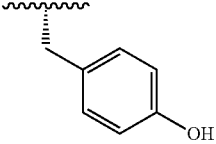 | 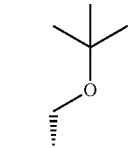 | 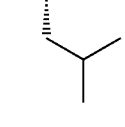 | 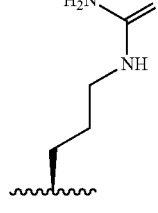 | Et |
| P13 | 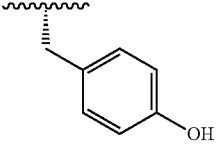 | 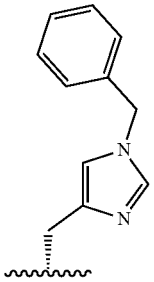 | 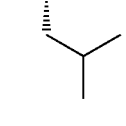 | 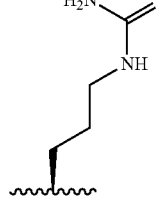 | Et |

-continued

| Proviso | R1 | R2 | R3 | R4 | R5 |
|---|---|---|---|---|---|
| P14 | 4-hydroxybenzyl | isobutyl | isobutyl | 4-guanidinobutyl | Et |
| P15 | 4-hydroxybenzyl | tert-butoxymethyl | isobutyl | 4-guanidinobutyl | NHCONH$_2$ |
| P16 | imidazol-4-ylmethyl | isobutyl | indol-3-ylmethyl | 4-hydroxybenzyl | NHCONH$_2$ |
| P17 | imidazol-4-ylmethyl | isobutyl | indol-3-ylmethyl | 4-hydroxybenzyl | Et |
| P18 | imidazol-4-ylmethyl | tert-butoxymethyl | indol-3-ylmethyl | 4-hydroxybenzyl | NHCONH$_2$ |
| P19 | imidazol-4-ylmethyl | tert-butoxymethyl | indol-3-ylmethyl | 4-hydroxybenzyl | Et |
| P20 | imidazol-4-ylmethyl | indol-3-ylmethyl | indol-3-ylmethyl | 4-hydroxybenzyl | NHCONH$_2$ |

-continued

| Proviso | R1 | R2 | R3 | R4 | R5 |
|---|---|---|---|---|---|
| P21 | imidazole (His) | indole-CH2 (Trp), NH | indole-CH2 (Trp) | 4-hydroxybenzyl (Tyr) | Et |

Disclaimed are compounds of formula (1) expressed as:
pGlu-His-Trp-Ser-$AA_1$-$AA_2$-$AA_3$-$AA_4$-Pro-X, where $AA_1$ is His, $AA_3$ is Trp, $AA_4$ is Tyr and $AA_2$ is selected from D-Leu, D-tBu-Ser and D-Trp, and X is —NHEt or NH—NH—$CONH_2$.

The compounds P1-P15 excluded from the invention can also be expressed as follows:

P1. pGlu-His-Trp-Ser-His-D-Ser(tBu)-Trp-Tyr-Pro-Gly-$NH_2$
P2. pGlu-His-Trp-Ser-His-D-Trp-Leu-Arg-Pro-Gly-$NH_2$
P3. pGlu-His-Trp-Ser-Tyr-D-Trp-Trp-Arg-Pro-Gly-N $H_2$
P4. pGlu-His-Trp-Ser-His-D-Trp-Trp-Arg-Pro-Gly-$NH_2$
P5. pGlu-His-Trp-Ser-Tyr-D-Trp-Trp-Tyr-Pro-Gly-$NH_2$
P6. pGlu-His-Trp-Ser-His-D-Trp-Trp-Tyr-Pro-Gly-$NH_2$
P7. pGlu-His-Trp-Ser-His-D-Trp-Trp-Tyr-Pro-NHEt
P8. pGlu-His-Trp-Ser-His-D-NaI-Trp-Tyr-Pro-NHEt
P9. pGlu-His-Trp-Ser-His-D-Leu-Trp-Tyr-Pro-Gly-$NH_2$
P10. pGlu-His-Trp-Ser-Tyr-D-Trp-Leu-Arg-Pro-Gly-$NH_2$
P11. pGlu-His-Trp-Ser-Tyr-D-NaI-Leu-Arg-Pro-Gly-$NH_2$
P12. pGlu-His-Trp-Ser-Tyr-D-Ser(tBu)-Leu-Arg-Pro-NHEt
P13. pGlu-His-Trp-Ser-Tyr-D-Bhi-Leu-Arg-Pro-NHEt
P14. pGlu-His-Trp-Ser-Tyr-D-Leu-Leu-Arg-Pro-NHEt
P15. pGlu-His-Trp-Ser-Tyr-D-Ser(tBu)-Leu-Arg-Pro-$NHNHCONH_2$

An interesting selection of compounds of the invention is compounds of Formula (I), or a pharmaceutically acceptable salt thereof, and wherein:

| Group | Type I | Type II |
|---|---|---|
| $R_1$ | 4-hydroxybenzyl | imidazolyl-methyl (His) |
| $R_3$ | isobutyl (Leu) | indol-3-ylmethyl (Trp) |
| $R_4$ | (CH2)3-NH-C(=NH)NH2 (Arg) | 4-hydroxybenzyl (Tyr) | and wherein at least one of $R_1$, $R_3$ and $R_4$ are selected from type II, and those of $R_1$, $R_3$ and $R_4$ which are not selected from type II, are selected from Type I, wherein $R_2$ = tBu-O-CH2 (Ser(tBu)), or indol-3-ylmethyl (Trp), or naphthalen-2-ylmethyl, or N-benzyl-imidazolylmethyl, or isobutyl (Leu)

and wherein $R_5$=Me, Et, $CH_2CF_3$, iPr, nPr, nBu, iBu, sBu, tBu, cyclopropyl or, $CH_2CONH_2$ This selection of compounds can also be expressed as:

pGlu-His-Trp-Ser-AA$_1$AA$_2$-AA$_3$-AA$_4$-Pro-X, wherein AA$_1$, AA$_2$, AA$_3$, AA$_4$ and X are as defined above and wherein at least one of AA$_1$, AA$_3$ and AA$_4$ is selected from His, Trp and Tyr; the remaining AA$_1$, AA$_3$ and AA$_4$ is selected from Tyr, Leu, Arg and with exclusion of the compounds P1-P15 as specified above and those other compounds disclaimed in claim 1.

In an embodiment, two or three of R$_1$, R$_3$ and R$_4$ are selected from type II according to the list above, and the remaining R$_1$, R$_3$ and R$_4$ are selected from type I.

In an embodiment one of R$_1$, R$_3$ and R$_4$ is selected from Type I according to the list above and two of R$_1$, R$_3$ and R$_4$ are selected from type II according to the list above.

Specific compounds according to the invention include:

| Compound no. | R1 | R2 | R3 | R4 | R5 |
|---|---|---|---|---|---|
| 1 | imidazolyl-CH$_2$– (His) | –CH$_2$–O–C(CH$_3$)$_3$ (Ser(tBu)) | isobutyl (Leu) | guanidinobutyl (Arg) | CH$_2$CONH$_2$ |
| | pGlu-His-Trp-Ser-His-D-Ser(tBu)-Leu-Arg-Pro-Gly-amide, | | | | |
| 2 | 4-hydroxybenzyl (Tyr) | –CH$_2$–O–C(CH$_3$)$_3$ (Ser(tBu)) | indol-3-ylmethyl (Trp) | guanidinobutyl (Arg) | CH$_2$CONH$_2$ |
| | pGlu-His-Trp-Ser-Tyr-D-Ser(tBu)-Trp-Arg-Pro-Gly-amide | | | | |
| 3 | 4-hydroxybenzyl (Tyr) | –CH$_2$–O–C(CH$_3$)$_3$ (Ser(tBu)) | isobutyl (Leu) | 4-hydroxybenzyl (Tyr) | CH$_2$CONH$_2$ |
| | pGlu-His-Trp-Ser-Tyr-D-Ser(tBu)-Leu-Tyr-Pro-Gly-amide | | | | |
| 4 | imidazolyl-CH$_2$– (His) | –CH$_2$–O–C(CH$_3$)$_3$ (Ser(tBu)) | indol-3-ylmethyl (Trp) | guanidinobutyl (Arg) | CH$_2$CONH$_2$ |
| | pGlu-His-Trp-Ser-His-D-Ser(tBu)-Trp-Arg-Pro-Gly-amide | | | | |
| 5 | imidazolyl-CH$_2$– (His) | –CH$_2$–O–C(CH$_3$)$_3$ (Ser(tBu)) | isobutyl (Leu) | 4-hydroxybenzyl (Tyr) | CH$_2$CONH$_2$ |
| | pGlu-His-Trp-Ser-His-D-Ser(tBu)-Leu-Tyr-Pro-Gly-amide | | | | |

-continued

| Compound no. | R1 | R2 | R3 | R4 | R5 |
|---|---|---|---|---|---|
| 6 | imidazole-CH2- | -CH2-O-tBu | isobutyl | -(CH2)3-NH-C(=NH)-NH2 | Et |
| | pGlu-His-Trp-Ser-His-D-Ser(tBu)-Leu-Arg-Pro-NHEt | | | | |
| 7 | 4-hydroxybenzyl | -CH2-O-tBu | indol-3-ylmethyl | 4-hydroxybenzyl | CH2CONH2 |
| | pGlu-His-Trp-Ser-Tyr-D-Ser(tBu)-Trp-Tyr-Pro-Gly-amide | | | | |
| 8 | 4-hydroxybenzyl | -CH2-O-tBu | indol-3-ylmethyl | -(CH2)3-NH-C(=NH)-NH2 | Et |
| | pGlu-His-Trp-Ser-Tyr-D-Ser(tBu)-Trp-Arg-Pro-NHEt | | | | |
| 9 | 4-hydroxybenzyl | -CH2-O-tBu | isobutyl | 4-hydroxybenzyl | Et |
| | pGlu-His-Trp-Ser-Tyr-D-Ser(tBu)-Leu-Tyr-Pro-NHEt | | | | |
| 10 | imidazole-CH2- | -CH2-O-tBu | indol-3-ylmethyl | -(CH2)3-NH-C(=NH)-NH2 | Et |
| | pGlu-His-Trp-Ser-His-D-Ser(tBu)-Trp-Arg-Pro-NHEt | | | | |
| 11 | imidazole-CH2- | -CH2-O-tBu | isobutyl | 4-hydroxybenzyl | Et |
| | pGlu-His-Trp-Ser-His-D-Ser(tBu)-Leu-Tyr-Pro-NHEt | | | | |

-continued

| Compound no. | R1 | R2 | R3 | R4 | R5 |
|---|---|---|---|---|---|
| 12 | 4-hydroxybenzyl (Tyr) | tBu-O-CH2 (Ser(tBu)) | indol-3-ylmethyl (Trp) | 4-hydroxybenzyl (Tyr) | Et | pGlu-His-Trp-Ser-Tyr-D-Ser(tBu)-Trp-Tyr-Pro-NHEt

| 13 | imidazol-4-ylmethyl (His) | tBu-O-CH2 (Ser(tBu)) | indol-3-ylmethyl (Trp) | 4-hydroxybenzyl (Tyr) | Et | pGlu-His-Trp-Ser-His-D-Ser(tBu)-Trp-Tyr-Pro-NHEt

| 14 | 4-hydroxybenzyl (Tyr) | indol-3-ylmethyl (Trp) | isobutyl (Leu) | 4-hydroxybenzyl (Tyr) | CH2CONH2 | pGlu-His-Trp-Ser-Tyr-D-Trp-Leu-Tyr-Pro-Gly-amide

| 15 | 4-hydroxybenzyl (Tyr) | indol-3-ylmethyl (Trp) | isobutyl (Leu) | guanidinopropyl (Arg) | Et | pGlu-His-Trp-Ser-Tyr-D-Trp-Leu-Arg-Pro-NHEt

| 16 | imidazol-4-ylmethyl (His) | indol-3-ylmethyl (Trp) | isobutyl (Leu) | 4-hydroxybenzyl (Tyr) | CH2CONH2 | pGlu-His-Trp-Ser-His-D-Trp-Leu-Tyr-Pro-Gly-amide

| 17 | imidazol-4-ylmethyl (His) | indol-3-ylmethyl (Trp) | isobutyl (Leu) | guanidinopropyl (Arg) | Et | pGlu-His-Trp-Ser-His-D-Trp-Leu-Arg-Pro-NHEt

-continued

| Compound no. | R1 | R2 | R3 | R4 | R5 |
|---|---|---|---|---|---|
| 18 | 4-hydroxybenzyl | indol-3-ylmethyl | indol-3-ylmethyl | 3-guanidinopropyl | Et |
| | pGlu-His-Trp-Ser-Tyr-D-Trp-Trp-Arg-Pro-NHEt | | | | |
| 19 | 4-hydroxybenzyl | indol-3-ylmethyl | isobutyl | 4-hydroxybenzyl | Et |
| | pGlu-His-Trp-Ser-Tyr-D-Trp-Leu-Tyr-Pro-NHEt | | | | |
| 20 | imidazol-4-ylmethyl | indol-3-ylmethyl | indol-3-ylmethyl | 3-guanidinopropyl | Et |
| | pGlu-His-Trp-Ser-His-D-Trp-Trp-Arg-Pro-NHEt | | | | |
| 21 | imidazol-4-ylmethyl | indol-3-ylmethyl | isobutyl | 4-hydroxybenzyl | Et |
| | pGlu-His-Trp-Ser-His-D-Trp-Leu-Tyr-Pro-NHEt | | | | |
| 22 | 4-hydroxybenzyl | indol-3-ylmethyl | indol-3-ylmethyl | 4-hydroxybenzyl | Et |
| | pGlu-His-Trp-Ser-Tyr-D-Trp-Trp-Tyr-Pro-NHEt | | | | |
| 23 | imidazol-4-ylmethyl | naphth-2-ylmethyl | isobutyl | 3-guanidinopropyl | CH$_2$CONH$_2$ |
| | pGlu-His-Trp-Ser-His-D-Nal-Leu-Arg-Pro-Gly-amide | | | | |

-continued

| Compound no. | R1 | R2 | R3 | R4 | R5 |
|---|---|---|---|---|---|
| 24 | 4-hydroxybenzyl | 2-naphthylmethyl | (1H-indol-3-yl)methyl | 3-guanidinopropyl | CH$_2$CONH$_2$ | pGlu-His-Trp-Ser-Tyr-D-Nal-Trp-Arg-Pro-Gly-amide

| 25 | 4-hydroxybenzyl | 2-naphthylmethyl | isobutyl | 4-hydroxybenzyl | CH$_2$CONH$_2$ | pGlu-His-Trp-Ser-Tyr-D-Nal-Leu-Tyr-Pro-Gly-amide

| 26 | 4-hydroxybenzyl | 2-naphthylmethyl | isobutyl | 3-guanidinopropyl | Et | pGlu-His-Trp-Ser-Tyr-D-Nal-Leu-Arg-Pro-NHEt

| 27 | (1H-imidazol-4-yl)methyl | 2-naphthylmethyl | (1H-indol-3-yl)methyl | 3-guanidinopropyl | CH$_2$CONH$_2$ | pGlu-His-Trp-Ser-His-D-Nal-Trp-Arg-Pro-Gly-amide

| 28 | (1H-imidazol-4-yl)methyl | 2-naphthylmethyl | isobutyl | 4-hydroxybenzyl | CH$_2$CONH$_2$ | pGlu-His-Trp-Ser-His-D-Nal-Leu-Tyr-Pro-Gly-amide

-continued
| Compound no. | R1 | R2 | R3 | R4 | R5 |
|---|---|---|---|---|---|
| 29 | 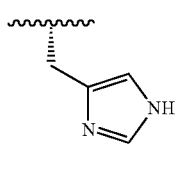 | 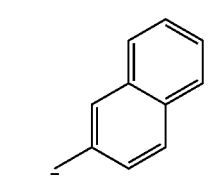 | 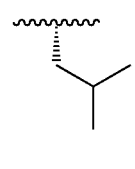 | 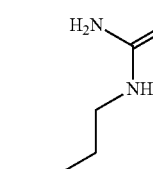 | Et |
pGlu-His-Trp-Ser-His-D-Nal-Leu-Arg-Pro-NHEt,
| 30 | 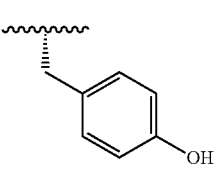 | 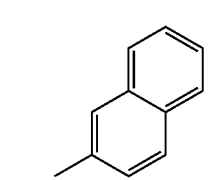 | 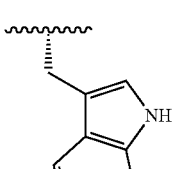 | 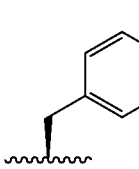 | $CH_2CONH_2$ |
pGlu-His-Trp-Ser-Tyr-D-Nal-Trp-Tyr-Pro-Gly-amide
| 31 | 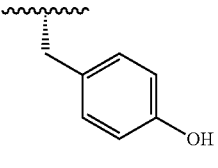 | 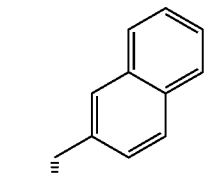 | 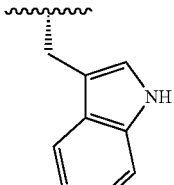 | 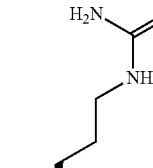 | Et |
pGlu-His-Trp-Ser-Tyr-D-Nal-Trp-Arg-Pro-NHEt
| 32 | 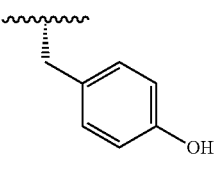 | 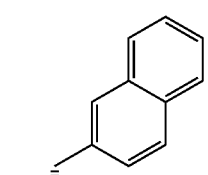 | 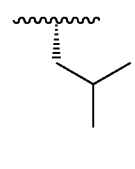 | 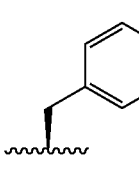 | Et |
pGlu-His-Trp-Ser-Tyr-D-Nal-Leu-Tyr-Pro-NHEt
| 33 | 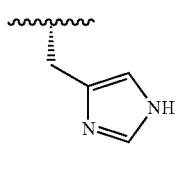 | 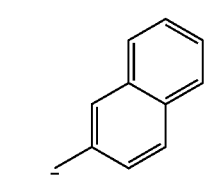 | 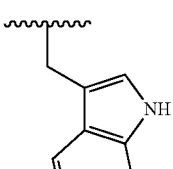 | 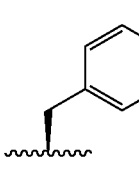 | $CH_2CONH_2$ |
pGlu-His-Trp-Ser-His-D-Nal-Trp-Tyr-Pro-Gly-amide -continued

| Compound no. | R1 | R2 | R3 | R4 | R5 |
|---|---|---|---|---|---|
| 34 | imidazole-CH₂- (His) | 2-naphthyl-CH₂- (Nal) | indol-3-yl-CH₂- (Trp) | guanidinopropyl- (Arg) | Et |
| | | | | pGlu-His-Trp-Ser-His-D-Nal-Trp-Arg-Pro-NHEt | |
| 35 | imidazole-CH₂- (His) | 2-naphthyl-CH₂- (Nal) | isobutyl- (Leu) | 4-hydroxybenzyl- (Tyr) | Et |
| | | | | pGlu-His-Trp-Ser-His-D-Nal-Leu-Tyr-Pro-NHEt | |
| 36 | 4-hydroxybenzyl- (Tyr) | 2-naphthyl-CH₂- (Nal) | indol-3-yl-CH₂- (Trp) | 4-hydroxybenzyl- (Tyr) | Et |
| | | | | pGlu-His-Trp-Ser-Tyr-D-Nal-Trp-Tyr-Pro-NHEt | |
| 37 | imidazole-CH₂- (His) | isobutyl- (Leu) | isobutyl- (Leu) | guanidinopropyl- (Arg) | CH₂CONH₂ |
| | | | | pGlu-His-Trp-Ser-His-D-Leu-Leu-Arg-Pro-Gly-amide | |
| 38 | 4-hydroxybenzyl- (Tyr) | isobutyl- (Leu) | indol-3-yl-CH₂- (Trp) | guanidinopropyl- (Arg) | CH₂CONH₂ |
| | | | | pGlu-His-Trp-Ser-Try-D-Leu-Trp-Arg-Pro-Gly-amide | |

-continued

| Compound no. | R1 | R2 | R3 | R4 | R5 |
| --- | --- | --- | --- | --- | --- |
| 39 | 4-hydroxybenzyl | isobutyl | isobutyl | 4-hydroxybenzyl | CH$_2$CONH$_2$ |
| | pGlu-His-Trp-Ser-Tyr-D-Leu-Leu-Tyr-Pro-Gly-amide | | | | |
| 40 | (1H-imidazol-4-yl)methyl | isobutyl | (1H-indol-3-yl)methyl | 3-guanidinopropyl | CH$_2$CONH$_2$ |
| | pGlu-His-Trp-Ser-His-D-Leu-Trp-Arg-Pro-Gly-amide | | | | |
| 41 | (1H-imidazol-4-yl)methyl | isobutyl | isobutyl | 4-hydroxybenzyl | CH$_2$CONH$_2$ |
| | pGlu-His-Trp-Ser-His-D-Leu-Leu-Tyr-Pro-Gly-amide | | | | |
| 42 | (1H-imidazol-4-yl)methyl | isobutyl | isobutyl | 3-guanidinopropyl | Et |
| | pGlu-His-Trp-Ser-His-D-Leu-Leu-Arg-Pro-NHEt | | | | |
| 43 | 4-hydroxybenzyl | isobutyl | (1H-indol-3-yl)methyl | 4-hydroxybenzyl | CH$_2$CONH$_2$ |
| | pGlu-His-Trp-Ser-Tyr-D-Leu-Trp-Tyr-Pro-Gly-amide | | | | |
| 44 | 4-hydroxybenzyl | isobutyl | (1H-indol-3-yl)methyl | 3-guanidinopropyl | Et |
| | pGlu-His-Trp-Ser-Tyr-D-Leu-Trp-Arg-Pro-NHEt | | | | |

-continued

| Compound no. | R1 | R2 | R3 | R4 | R5 |
|---|---|---|---|---|---|
| 45 | 4-hydroxybenzyl | isobutyl | isobutyl | 4-hydroxybenzyl | Et |
| | pGlu-His-Trp-Ser-Tyr-D-Leu-Leu-Tyr-Pro-NHEt | | | | |
| 46 | imidazol-4-ylmethyl | isobutyl | indol-3-ylmethyl | 4-hydroxybenzyl | CH$_2$CONH$_2$ |
| | pGlu-His-Trp-Ser-His-D-Leu-Trp-Tyr-Pro-Gly-amide | | | | |
| 47 | imidazol-4-ylmethyl | isobutyl | indol-3-ylmethyl | 3-guanidinopropyl | Et |
| | pGlu-His-Trp-Ser-His-D-Leu-Trp-Arg-Pro-NHEt | | | | |
| 48 | imidazol-4-ylmethyl | isobutyl | isobutyl | 4-hydroxybenzyl | Et |
| | pGlu-His-Trp-Ser-His-D-Leu-Leu-Tyr-Pro-NHEt | | | | |
| 49 | 4-hydroxybenzyl | isobutyl | indol-3-ylmethyl | 4-hydroxybenzyl | Et |
| | pGlu-His-Trp-Ser-Tyr-D-Leu-Trp-Tyr-Pro-NHEt | | | | |
| 50 | imidazol-4-ylmethyl | isobutyl | indol-3-ylmethyl | 4-hydroxybenzyl | Et |
| | pGlu-His-Trp-Ser-His-D-Leu-Trp-Tyr-Pro-NHEt | | | | |

-continued
| Compound no. | R1 | R2 | R3 | R4 | R5 |
|---|---|---|---|---|---|
| 51 | | | | | CH₂CONH₂ |
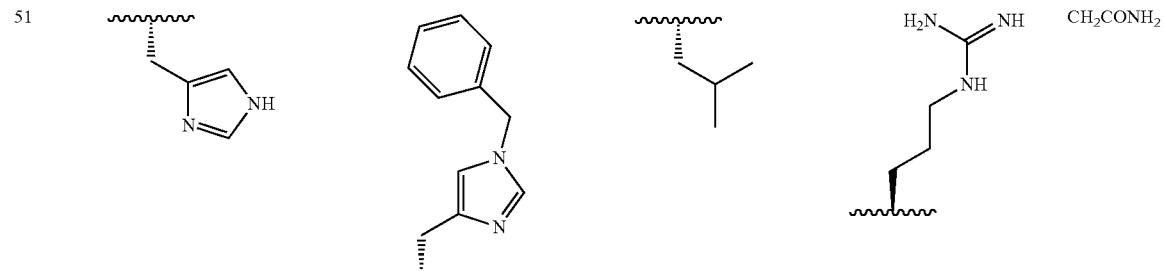
pGlu-His-Trp-Ser-His-D-Bhi-Leu-Arg-Pro-Gly-amide
| 52 | | | | | CH₂CONH₂ |
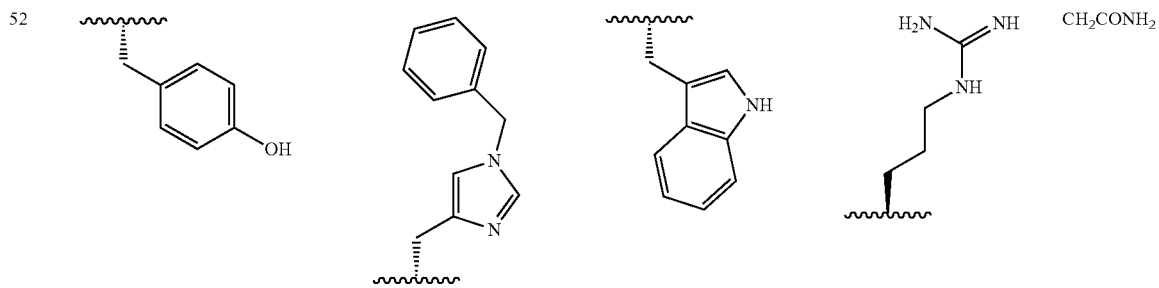
pGlu-His-Trp-Ser-Tyr-D-Bhi-Trp-Arg-Pro-Gly-amide
| 53 | | | | | CH₂CONH₂ |
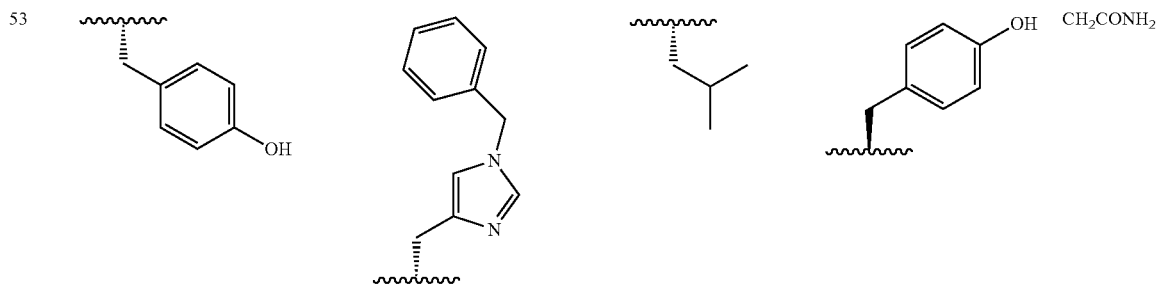
pGlu-His-Trp-Ser-Tyr-D-Bhi-Leu-Tyr-Pro-Gly-amide
| 54 | | | | | CH₂CONH₂ |
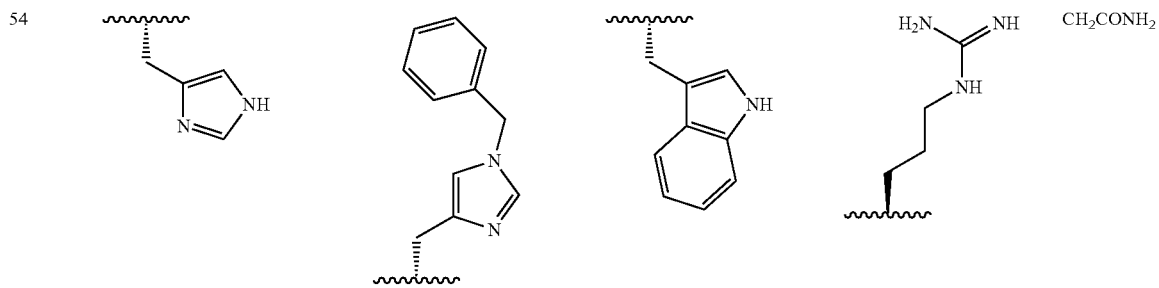
pGlu-His-Trp-Ser-His-D-Bhi-Trp-Arg-Pro-Gly-amide -continued

| Compound no. | R1 | R2 | R3 | R4 | R5 |
|---|---|---|---|---|---|
| 55 | 4-imidazolylmethyl (His side chain) | 1-benzyl-4-imidazolylmethyl | isobutyl | 4-hydroxybenzyl (Tyr side chain) | CH₂CONH₂ | pGlu-His-Trp-Ser-His-D-Bhi-Leu-Try-Pro-Gly-amide

| 56 | 4-imidazolylmethyl (His side chain) | 1-benzyl-4-imidazolylmethyl | isobutyl | guanidinopropyl (Arg side chain) | Et | pGlu-His-Trp-Ser-His-D-Bhi-Leu-Arg-Pro-NHEt

| 57 | 4-hydroxybenzyl (Tyr side chain) | 1-benzyl-4-imidazolylmethyl | 3-indolylmethyl (Trp side chain) | guanidinopropyl (Arg side chain) | CH₂CONH₂ | pGlu-His-Trp-Ser-Tyr-D-Bhi-Trp-Arg-Pro-Gly-amide

| 58 | 4-hydroxybenzyl (Tyr side chain) | 1-benzyl-4-imidazolylmethyl | 3-indolylmethyl (Trp side chain) | guanidinopropyl (Arg side chain) | CH₂CONH₂ | pGlu-His-Trp-Ser-Tyr-D-Bhi-Trp-Arg-Pro-Gly-amide

-continued

| Compound no. | R1 | R2 | R3 | R4 | R5 |
|---|---|---|---|---|---|
| 59 | 4-hydroxybenzyl | benzyl-imidazolyl-methyl | isobutyl | 4-hydroxybenzyl | Et |
| | | pGlu-His-Trp-Ser-Tyr-D-Bhi-Leu-Tyr-Pro-NHEt | | | |
| 60 | imidazolyl-methyl | benzyl-imidazolyl-methyl | indol-3-yl-methyl | 3-guanidinopropyl | Et |
| | | pGlu-His-Trp-Ser-His-D-Bhi-Trp-Arg-Pro-NHEt | | | |
| 61 | imidazolyl-methyl | benzyl-imidazolyl-methyl | isobutyl | 4-hydroxybenzyl | Et |
| | | pGlu-His-Trp-Ser-His-D-Bhi-Leu-Tyr-Pro-NHEt | | | |
| 62 | 4-hydroxybenzyl | benzyl-imidazolyl-methyl | indol-3-yl-methyl | 4-hydroxybenzyl | Et |
| | | pGlu-His-Trp-Ser-Tyr-D-Bhi-Trp-Tyr-Pro-NHEt | | | |

| Compound no. | R1 | R2 | R3 | R4 | R5 |
|---|---|---|---|---|---|
| 63 | (imidazole-CH2-, His) | (1-benzyl-imidazole-CH2-, Bhi) | (indole-CH2-, Trp) | (4-hydroxybenzyl-, Tyr) | Et |
| | pGlu-His-Trp-Ser-His-D-Bhi-Trp-Tyr-Pro-NHEt | | | | |
| 64 | (4-hydroxybenzyl-, Tyr) | (indole-CH2-, Trp) | (indole-CH2-, Trp) | (4-hydroxybenzyl-, Tyr) | CH2CONH2 |
| | pGlu-His-Trp-Ser-Tyr-D-Trp-Trp-Tyr-Pro-Gly-amide | | | | |
| 65 | (imidazole-CH2-, His) | (indole-CH2-, Trp) | (indole-CH2-, Trp) | (4-hydroxybenzyl-, Tyr) | CH2CONH2 |
| | pGlu-His-Trp-Ser-His-D-Trp-Trp-Tyr-Pro-Gly-amide | | | | |
| 66 | (4-hydroxybenzyl-, Tyr) | (indole-CH2-, Trp) | (indole-CH2-, Trp) | (guanidino-propyl-, Arg) | CH2CONH2 |
| | pGlu-His-Trp-Ser-Tyr-D-Trp-Trp-Arg-Pro-Gly-amide | | | | |
| 67 | (4-hydroxybenzyl-, Tyr) | (1-benzyl-imidazole-CH2-, Bhi) | (indole-CH2-, Trp) | (guanidino-propyl-, Arg) | Et |
| | pGlu-His-Trp-Ser-Tyr-D-Bhi-Trp-Arg-Pro-NHEt | | | | |

| Compound no. | R1 | R2 | R3 | R4 | R5 |
|---|---|---|---|---|---|
| 68 | | | | | CH$_2$CONH$_2$ |

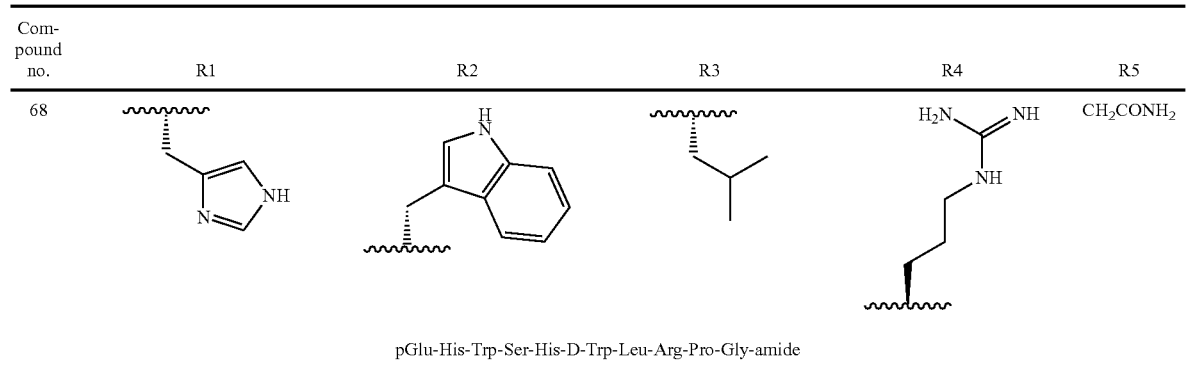

pGlu-His-Trp-Ser-His-D-Trp-Leu-Arg-Pro-Gly-amide

Of particular interest are compounds that are GnRH II analogues predominantly having i) stimulating effect on or ii) affinity for GnRH II receptor. Thus, compounds are preferred that do not bind to or activate GnRH I receptor resulting in an undesired therapeutic response. It is contemplated that GnRH II analogues that do bind to or activate type I GnRH receptor thereby stimulating endocrine signalling are administered together with a sex hormone to counter endocrine effects.

General Chemistry Methods

The skilled person will recognise that the compounds of the invention may be prepared, in known manner, in a variety of ways. The routes below are merely illustrative of some methods that can be employed for the synthesis of compounds of formula (I).

In general, synthetic methods for preparing compounds of the invention can be divided into two methods: liquid phase synthesis and solid phase synthesis. Liquid phase peptide synthesis involves reagents reacting together in the solution phase. Disadvantages of this method include difficulty in separating and purification of the products. Solid phase peptide synthesis is more common and has numerous advantages including convenient isolation and purification and applicability to automation (Bodanszky et al, In Peptide Synthesis, John Wiley & Sons, 1976). Many peptide synthetic resins have been developed to allow synthesis of various peptides. These include chloromethyl and 2-chlorotityl polystyrene resins. Examples of patents disclosing methods for synthesis of short peptides include U.S. Pat. No. 5,602,231, EP 0518655 and U.S. Pat. No. 6,879,289.

When a compound of the invention is prepared with a C-terminal secondary amide, as in e.g. buserelin, then one method of preparing the compounds is as follows and depicted in scheme I below. The peptide can be assembled on a solid support, typically 2-chlorotrityl polystyrene resin is used, but others will be apparent to one skilled in the art. The first amino acid is loaded and then deprotected to reveal a reactive amine group that is then used to couple onto the next amino acid. This in turn can be deprotected and coupled. After multiple rounds of extension, the desired peptide sequence is obtained. The peptide is then cleaved from the resin by the action of TFA or similar reagents. Note that when a tert-butyl side chain is required in the final compound it is important to keep the reaction time low enough such that this does not cleave entirely. Some tert-butyl will cleave but this can be removed in purification. Finally, the secondary amide is prepared by coupling the deprotected peptide at the C-terminus with a selected primary amine. Coupling reactions typically utilise HBTU and DIPEA, though one skilled in the art will be able to identify other activators and bases that can be used in combination to effect the amide bond formation.

Scheme I

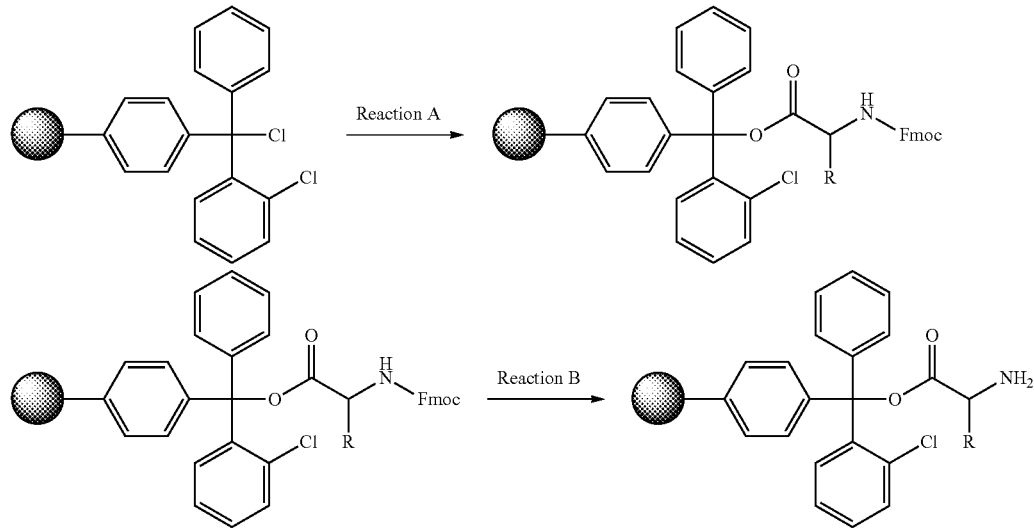

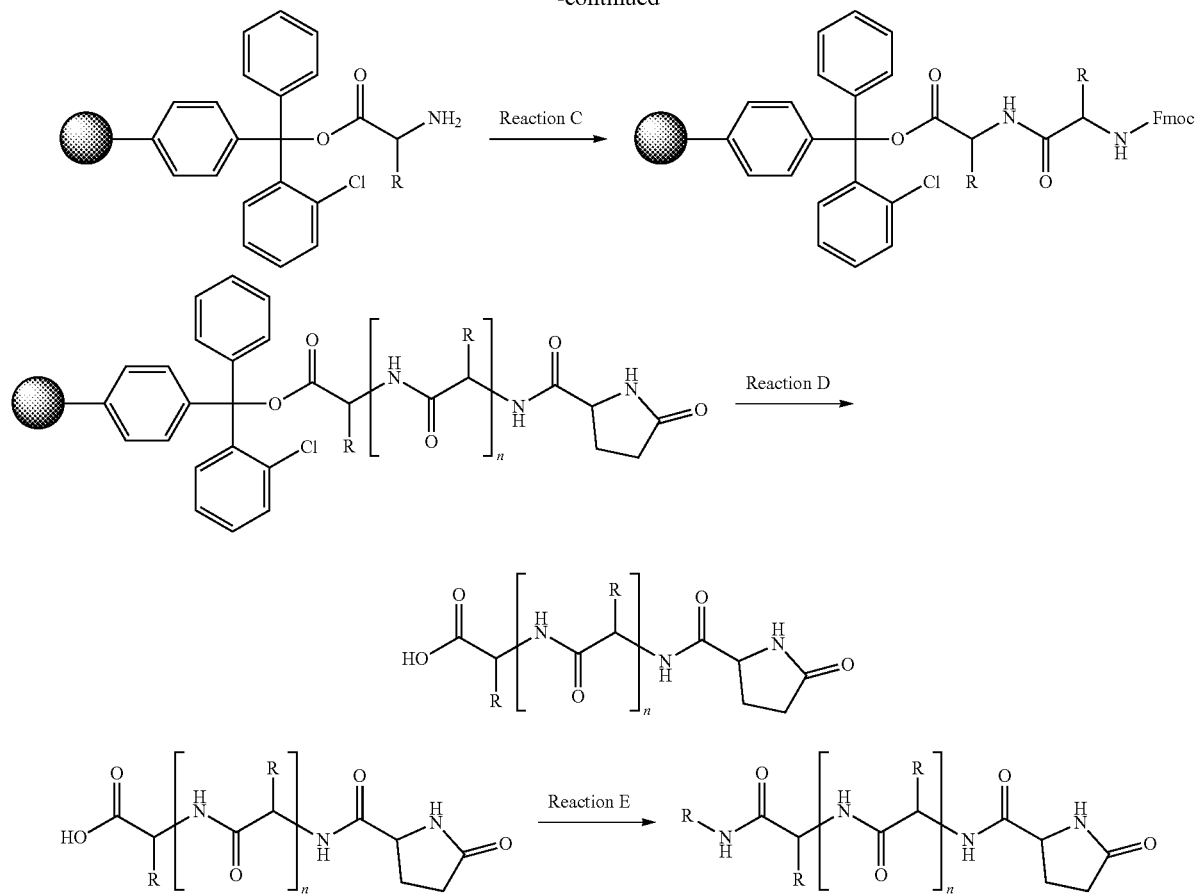

When a compound of the invention is prepared with a C-terminal primary amide, as in e.g. triptorelin, then one method of preparing the compounds is as follows and depicted in scheme II below. The peptide can be assembled on a solid support, typically Ramage resin is used, but others will be apparent to one skilled in the art. The first amino acid is loaded and then deprotected to reveal a reactive amine group that is then used to couple onto the next amino acid. This in turn can be deprotected and coupled. After multiple rounds of extension, the desired peptide sequence is obtained. The peptide is then cleaved from the resin by the action of TFA or similar reagents. Coupling reactions typically utilise HBTU and DIPEA, though one skilled in the art will be able to identify other activators and bases that can be used in combination to effect the amide bond formation.

Scheme II

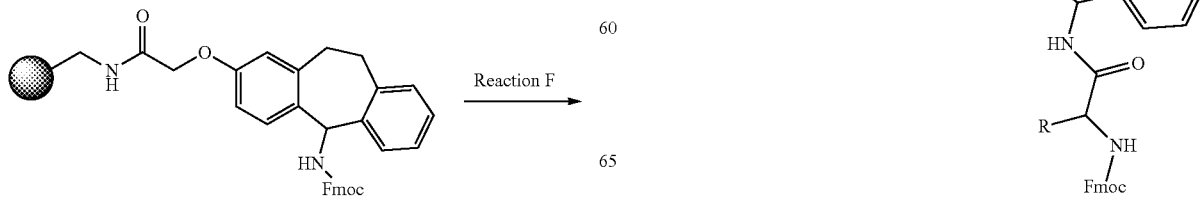

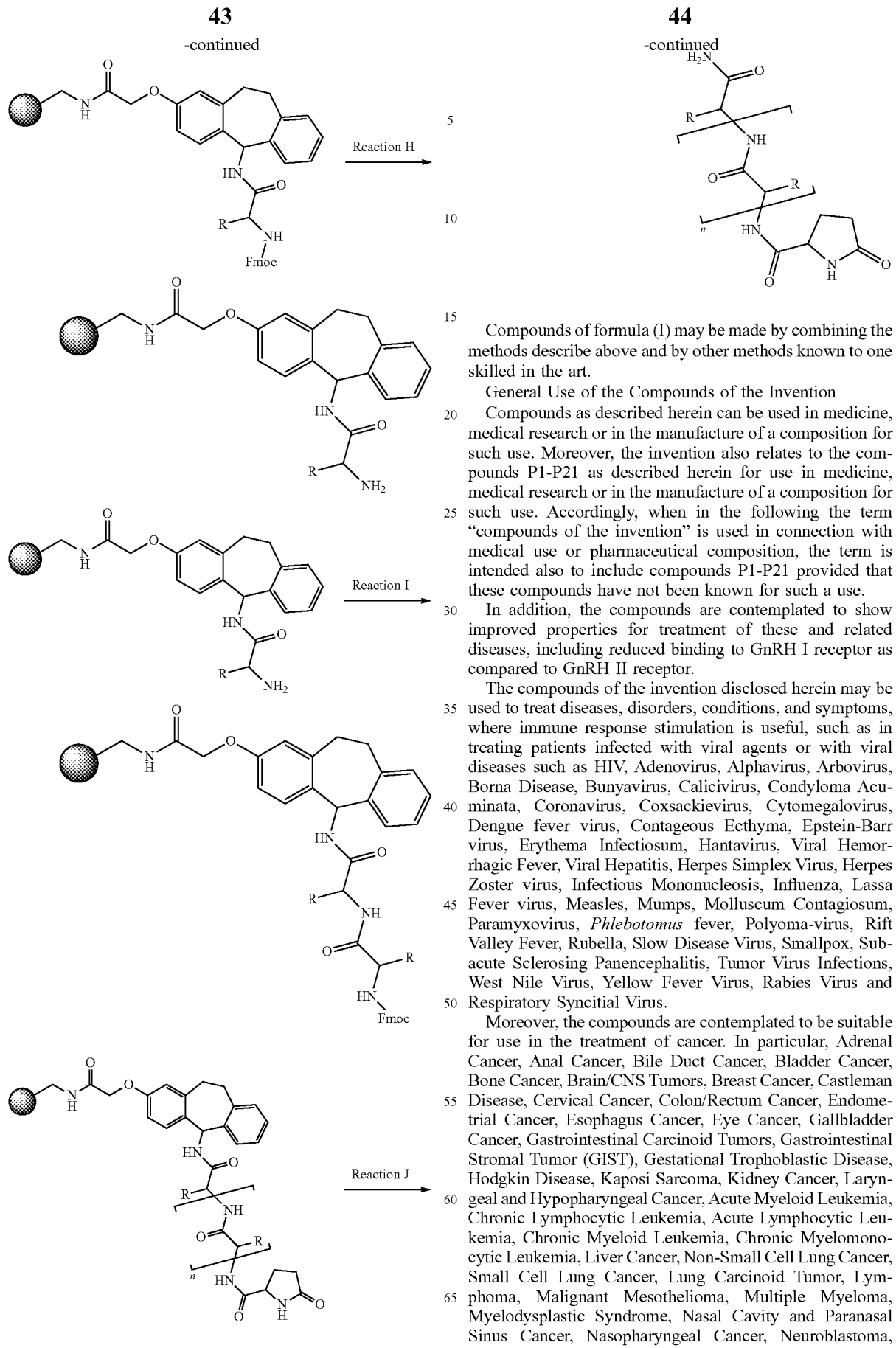

Compounds of formula (I) may be made by combining the methods describe above and by other methods known to one skilled in the art.

General Use of the Compounds of the Invention

Compounds as described herein can be used in medicine, medical research or in the manufacture of a composition for such use. Moreover, the invention also relates to the compounds P1-P21 as described herein for use in medicine, medical research or in the manufacture of a composition for such use. Accordingly, when in the following the term "compounds of the invention" is used in connection with medical use or pharmaceutical composition, the term is intended also to include compounds P1-P21 provided that these compounds have not been known for such a use.

In addition, the compounds are contemplated to show improved properties for treatment of these and related diseases, including reduced binding to GnRH I receptor as compared to GnRH II receptor.

The compounds of the invention disclosed herein may be used to treat diseases, disorders, conditions, and symptoms, where immune response stimulation is useful, such as in treating patients infected with viral agents or with viral diseases such as HIV, Adenovirus, Alphavirus, Arbovirus, Borna Disease, Bunyavirus, Calicivirus, Condyloma Acuminata, Coronavirus, Coxsackievirus, Cytomegalovirus, Dengue fever virus, Contageous Ecthyma, Epstein-Barr virus, Erythema Infectiosum, Hantavirus, Viral Hemorrhagic Fever, Viral Hepatitis, Herpes Simplex Virus, Herpes Zoster virus, Infectious Mononucleosis, Influenza, Lassa Fever virus, Measles, Mumps, Molluscum Contagiosum, Paramyxovirus, *Phlebotomus* fever, Polyoma-virus, Rift Valley Fever, Rubella, Slow Disease Virus, Smallpox, Subacute Sclerosing Panencephalitis, Tumor Virus Infections, West Nile Virus, Yellow Fever Virus, Rabies Virus and Respiratory Syncitial Virus.

Moreover, the compounds are contemplated to be suitable for use in the treatment of cancer. In particular, Adrenal Cancer, Anal Cancer, Bile Duct Cancer, Bladder Cancer, Bone Cancer, Brain/CNS Tumors, Breast Cancer, Castleman Disease, Cervical Cancer, Colon/Rectum Cancer, Endometrial Cancer, Esophagus Cancer, Eye Cancer, Gallbladder Cancer, Gastrointestinal Carcinoid Tumors, Gastrointestinal Stromal Tumor (GIST), Gestational Trophoblastic Disease, Hodgkin Disease, Kaposi Sarcoma, Kidney Cancer, Laryngeal and Hypopharyngeal Cancer, Acute Myeloid Leukemia, Chronic Lymphocytic Leukemia, Acute Lymphocytic Leukemia, Chronic Myeloid Leukemia, Chronic Myelomonocytic Leukemia, Liver Cancer, Non-Small Cell Lung Cancer, Small Cell Lung Cancer, Lung Carcinoid Tumor, Lymphoma, Malignant Mesothelioma, Multiple Myeloma, Myelodysplastic Syndrome, Nasal Cavity and Paranasal Sinus Cancer, Nasopharyngeal Cancer, Neuroblastoma, Non-Hodgkin Lymphoma, Oral Cavity and Oropharyngeal Cancer, Osteosarcoma, Ovarian Cancer, Pancreatic Cancer, Penile Cancer, Pituitary Tumors, Prostate Cancer, Retinoblastoma, Rhabdomyosarcoma, Salivary Gland Cancer, Basal and Squamous Cell Skin Cancer, Melanoma, Merkel Cell Skin Cancer, Small Intestine Cancer, Stomach Cancer, Testicular Cancer, Thymus Cancer, Thyroid Cancer, Uterine Sarcoma, Vaginal Cancer, Vulvar Cancer, Waldenstrom Macroglobulinemia, Wilms Tumor.

Thus the advantageous properties of the compound of the invention may include one or more of the following:

Improved binding to GnRH II receptor as compared to GnRH I receptor
Improved MHC class I stimulation
Improved immunomodulation
Improved activation of antigen presenting cells
Improved T-cell response
Improved antiviral activity
Improved anticancer activity Pharmaceutical Compositions Comprising a Compound of the Invention The present invention also provides a pharmaceutical composition comprising the compound of the invention together with one or more pharmaceutically acceptable diluents or carriers. The present chapter is primarily directed to formulation of the novel GnRH analogs. In those cases where the novel compounds have an effect on type I GnRH receptor, which is unwanted and causes castration or similar effects, compositions containing sex hormones are known in the art and may be co-administered.

The compounds of the invention or a formulation thereof may be administered by any conventional route for example but without limitation it may be administered parenterally, orally, topically or via a mucosa (including buccal, sublingual, transdermal, vaginal, rectal, nasal, ocular etc.), via a medical device (e.g. a stent), by inhalation. The treatment may consist of a single administration or a plurality of administrations over a period of time.

The treatment may be by administration once daily, twice daily, three times daily, four times daily etc. dependent on the specific disease to be treated and the weight and age of the patient to be treated. The treatment may also be by continuous administration such as e.g. administration intravenous by infusion via a drop.

Whilst it is possible for the compound of the invention to be administered as such, it is preferable to present it as a pharmaceutical formulation, together with one or more acceptable carriers. The carrier(s) must be "acceptable" in the sense of being compatible with the compound of the invention and not deleterious to the recipients thereof. Examples of suitable carriers are described in more detail below.

The formulations may conveniently be presented in a suitable dosage form including a unit dosage form and may be prepared by any of the methods well known in the art of pharmacy. Such methods include the step of bringing into association the active ingredient (compound of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

The compound of the invention will normally be administered by any conventional administration route normally by the oral or any parenteral route, in the form of a pharmaceutical formulation comprising the active ingredient, optionally in the form of a nontoxic organic, or inorganic, acid, or base, addition salt, in a pharmaceutically acceptable dosage form. Depending upon the disorder and patient to be treated, as well as the route of administration, the compositions may be administered at varying doses and/or frequencies.

The pharmaceutical compositions must be stable under the conditions of manufacture and storage; thus, if necessary should be preserved against the contaminating action of microorganisms such as bacteria and fungi. In case of liquid formulations such as solutions, dispersion, emulsions and suspensions, the carrier can be a solvent or dispersion medium containing, for example, water, ethanol, polyol (e.g. glycerol, propylene glycol and liquid polyethylene glycol), vegetable oils, and suitable mixtures thereof.

For example, the compound of the invention may be administered orally, buccally or sublingually in the form of tablets, capsules, films, ovules, elixirs, solutions, emulsions or suspensions, which may contain flavouring or colouring agents.

Formulations in accordance with the present invention suitable for oral administration may be presented as discrete units such as capsules, cachets or tablets, each containing a predetermined amount of the active ingredient; as multiple units e.g. in the form of a tablet or capsule: as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Solutions or suspensions of the compound of the invention suitable for oral administration may also contain one or more solvents including water, alcohol, polyol etc. as well as one or more excipients such as pH-adjusting agent, stabilizing agents, surfactants, solubilizers, dispersing agents, preservatives, flavors etc. Specific examples include e.g. N,N-dimethylacetamide, dispersants e.g. polysorbate 80, surfactants, and solubilisers, e.g. polyethylene glycol, Phosal 50 PG (which consists of phosphatidylcholine, soya-fatty acids, ethanol, mono/diglycerides, propylene glycol and ascorbyl palmitate). The formulations according to present invention may also be in the form of emulsions, wherein a compound according to Formula (I) may be present in an emulsion such as an oil-in-water emulsion or a water-in-oil emulsion. The oil may be a natural or synthetic oil or any oil-like substance such as e.g. soy bean oil or safflower oil or combinations thereof.

Tablets may contain excipients such as microcrystalline cellulose, lactose (e.g. lactose monohydrate or lactose anyhydrous), sodium citrate, calcium carbonate, dibasic calcium phosphate and glycine, butylated hydroxytoluene (E321), crospovidone, hypromellose, disintegrants such as starch (preferably corn, potato or tapioca starch), sodium starch glycollate, croscarmellose sodium, and certain complex silicates, and granulation binders such as polyvinylpyrrolidone, hydroxypropylmethylcellulose (HPMC), hydroxy-propylcellulose (HPC), macrogol 8000, sucrose, gelatin and acacia. Additionally, lubricating agents such as magnesium stearate, stearic acid, glyceryl behenate and talc may be included.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Pharmaceutical compositions adapted for topical administration may be formulated as ointments, creams, suspensions, lotions, powders, solutions, pastes, gels, impregnated dressings, sprays, aerosols or oils, transdermal devices, dusting powders, and the like. These compositions may be prepared via conventional methods containing the active agent. Thus, they may also comprise compatible conventional carriers and additives, such as preservatives, solvents to assist drug penetration, emollient in creams or ointments and ethanol or oleyl alcohol for lotions. Such carriers may be present as from about 1% up to about 98% of the composition. More usually they will form up to about 80% of the composition. As an illustration only, a cream or ointment is prepared by mixing sufficient quantities of hydrophilic material and water, containing from about 5-10% by weight of the compound, in sufficient quantities to produce a cream or ointment having the desired consistency.

Pharmaceutical compositions adapted for transdermal administration may be presented as discrete patches intended to remain in intimate contact with the epidermis of the recipient for a prolonged period of time. For example, the active agent may be delivered from the patch by iontophoresis.

For applications to external tissues, for example the mouth and skin, the compositions are preferably applied as a topical ointment or cream. When formulated in an ointment, the active agent may be employed with either a paraffinic or a water-miscible ointment base.

Alternatively, the active agent may be formulated in a cream with an oil-in-water cream base or a water-in-oil base.

For parenteral administration, fluid unit dosage forms are prepared utilizing the active ingredient and a sterile vehicle, for example but without limitation water, alcohols, polyols, glycerine and vegetable oils, water being preferred. The active ingredient, depending on the vehicle and concentration used, can be either colloidal, suspended or dissolved in the vehicle. In preparing solutions the active ingredient can be dissolved in water for injection and filter sterilised before filling into a suitable vial or ampoule and sealing.

Advantageously, agents such as local anaesthetics, preservatives and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability.

Parenteral suspensions are prepared in substantially the same manner as solutions, except that the active ingredient is suspended in the vehicle instead of being dissolved and sterilization cannot be accomplished by filtration. The active ingredient can be sterilised by exposure to ethylene oxide before suspending in the sterile vehicle. Advantageously, a surfactant or wetting agent is included in the composition to facilitate uniform distribution of the active ingredient.

It should be understood that in addition to the ingredients particularly mentioned above the formulations of this invention may include other agents conventional in the art having regard to the type of formulation in question, for example those suitable for oral administration may include flavouring agents. A person skilled in the art will know how to choose a suitable formulation and how to prepare it (see eg Remington's Pharmaceutical Sciences 18 Ed. or later). A person skilled in the art will also know how to choose a suitable administration route and dosage.

It will be recognized by one of skill in the art that the optimal quantity and spacing of individual dosages of a compound of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

All % values mentioned herein are % w/w unless the context requires otherwise.

Sequence List

The sequence list is prepared according to the WIPO standard ST.25. In the sequence list, the unnatural amino acids of compounds 1-63 and P1-P21 are represented as the corresponding natural amino acid in the following way:

| Unnatural amino acid | Corresponding natural amino acid |
|---|---|
| pGlu, pyroglutamate | L-Glutamate, Glu |
| 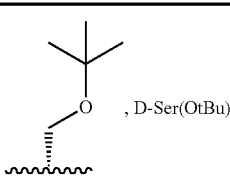, D-Ser(OtBu) | L-Serine, Ser |
| 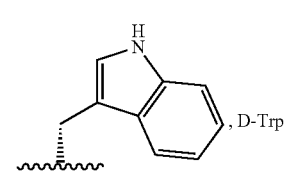, D-Trp | L-Tryptophan, Trp |

-continued

| Unnatural amino acid | Corresponding natural amino acid |
|---|---|
| pGlu, pyroglutamate | L-Glutamate, Glu |
| D-Nal (2-naphthylmethyl structure) | L-Phenylalanine, Phe |
| D-Bhi (N-benzyl-imidazole structure) | L-Histidine, His |
| D-Leu (isobutyl structure) | L-Leucin, Leu |
| Pro-Et | L-Proline, Pro |
| Pro-NHNHCONH₂ | L-Proline, Pro |
| Gly-NH₂ | Gly |

In the sequence list, entries 1-63 correspond to compounds 1-63, and entries 64-78 correspond to compounds P1-P15. Entries 79 and 80 correspond to wild-type GnRH I and GnRH II. Entries 81-84 correspond to primers. Entries 85-89 correspond to compounds 64-68. Entries 90-95 correspond to compounds P16-P21. However, the sequences SEQ ID Nos: 1-78 and 85-89 as they are stated in the sequence list, i.e. without above-described unnatural amino acids, are not claimed, but are included only to comply with the requirements of R. 30(1) of the EPC.

Repetition of Free Text from Sequence Listing

For compliance with paragraph 36 of WIPO Standard ST.25, the free text included under numeric identifier <223> of the sequence listing is hereby repeated in the main part of the description:

| SEQ ID NO | Free text included in <223> |
|---|---|
| 1-78 | Man-made analogue of GnRH II |
| 79 | GnRH I |
| 80 | GnRH II |
| 81 | Type I GnRH Receptor forward primer |
| 82 | Type I GnRH Receptor reverse primer |
| 83 | Type II GnRH Receptor forward primer |
| 84 | Type II GnRH Receptor reverse primer |
| 85-95 | Man-made analogue of GnRH II |

Definitions

The articles "a" and "an" are used herein to refer to one or to more than one (i.e. at least one) of the grammatical objects of the article. By way of example "an analogue" means one analogue or more than one analogue.

As used herein the terms "immunorhelins" and "compound(s) of the invention" are used interchangeably and refer to compounds of formula (I).

The pharmaceutically acceptable salts of the compound of the invention include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

LEGENDS TO FIGURES

FIG. 1: Expression of MHC class I after stimulation of T cells with increasing concentrations of GnRH II. PBMCs from a healthy donor was stimulated with GnRH II and IL-2 for 72 hours. Data points represent mean fluorescent intensity of MCH class I expression on $CD4^+$ T cells (blue triangles) or $CD8^+$ T cells (black squares) measured with flow cytometry.

Figure 2A:
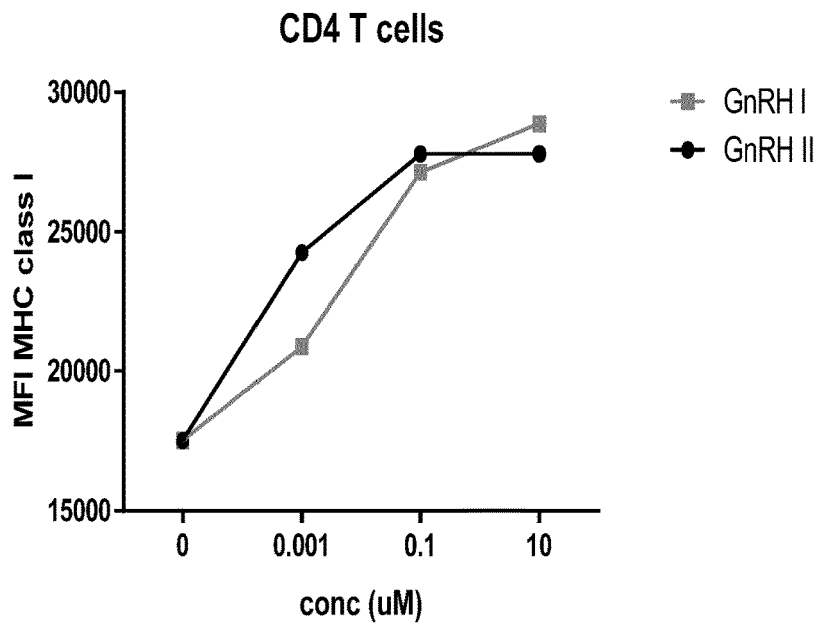
Figure 2B:
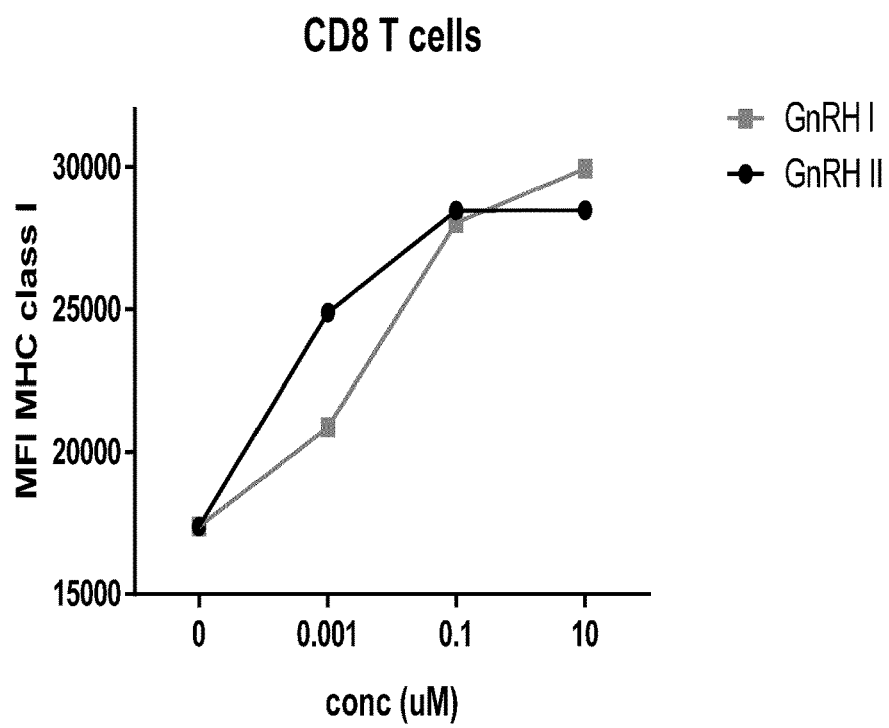

FIG. 2: Expression of MHC class I after stimulation of T cells with increasing concentrations of GnRH I analogoue (red) and GnRH II. (black). PBMCs from a healthy donor was stimulated with GnRH I analogoue or with GnRH II and IL-2 for 72 hours. Data points represent mean fluorescent intensity of MCH class I expression on $CD4^+$ T cells (A) or $CD8^+$ T cells (B) measured with flow cytometry.

Figure 3:
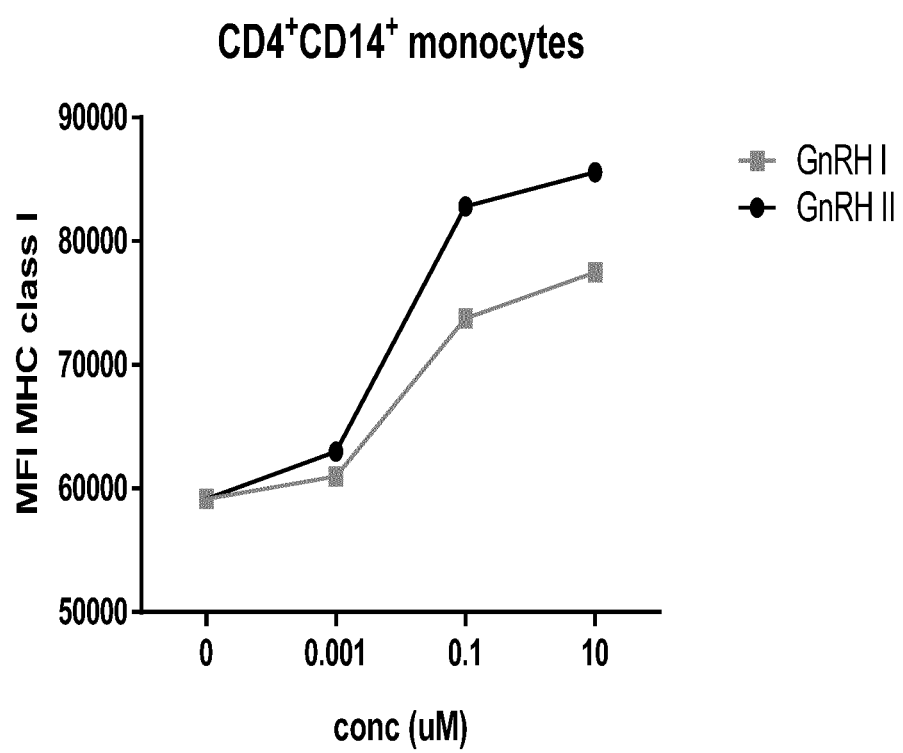

FIG. 3: Expression of MHC class I after stimulation of $CD4^+CD14^+$ monocytes with increasing concentrations of GnRH I analogue (red) and GnRH II (black). $CD14^+$ monocytes PBMCs from a healthy donor was stimulated with GnRH I analogue or with GnRH II and IL-2 for 72 hours. Data points represent mean fluorescent intensity of MCH class I expression on $CD4^+CD14^+$ monocytes measured with flow cytometry.

FIG. 4: GnRH receptor expression in human T cells analysed with quantitative real-time PCR. The bars represent ratios of GnRHR I or GnRHR II mRNA normalized to RNA polymerase II expression in sorted naive T cells (white bars) or memory T cells (gray bars). MCF-7 breast cancer cell line (black bar) was used as a positive control.

EXPERIMENTAL

General Biology Methods

The preferential effect of the compounds of the invention on GnRH receptors may be tested using one or more of the methods described below:

I. Expression of GnRH Receptors on T Cells

Human naive and memory T cells were labeled with fluorescent surface marker antibodies CD45RA, CD45RO and CD4 and sorted with flow cytometry. Total RNA was extracted with Rnaeasy kit (Qiagen) and reversed transcribed with iScript select cDNA synthesis kit (Biorad). The template cDNA was amplified with SYBR Green (Applied Biosystem) and run on CFX96 PCR (Biorad). Ratios of Type I GnRH Receptor and Type II GnRH Receptor mRNA were normalized to RNA polymerase II expression in sorted naive T cells or memory T cells. The MCF-7 breast cancer cell line was used as a positive control.

Primer Sequences:

```
Type I GnRH Receptor
  fwd 5'-tgc ctc ttc atc atc cct ct-3'
  rev 5'-gca aat gca acc gtc att tt-3'

Type II GnRH Receptor
  fwd 5'-act gtt caa tgg ctg gct gt-3'
  rev 5'-gcc ccc aga agt ttc ctt ac-3'
```

I. GnRH I Vs GnRH II Assay

Compounds were tested on cells made to express Type I or Type II GnRH Receptors by transfection. The cells were exposed to labelled GnRH compound, washed and then assessed by measuring the label on the cells. The label was either measured directly (radioactive isotope label or fluorescent label) or indirectly (biotin labelled peptide).

Signalling induced by the GnRH compounds was measured in the cell lines expressing Type I GnRH and Type II GnRH Receptors respectively. GnRH compounds were investigated for their respective affinity to GnRH I and GnRH II receptors using competition assays. Calcium flux was measured using cells labelled with Fluo-4-Direct either using a flow cytometer or by live cell imaging microscopy, in order to evaluate their potency establishing ED50 values. Signalling was also studied by western blotting using antibodies to p-ERK or p-JNK.

To assess the effects of cellular activation on the production of LH and FSH and compare it with stimulation of immune related functions, the effects of the compounds were studied on pituitary cells and immune cells expressing either Type II GnRH or Type I GnRH Receptors.

II. Immune Stimulation Assay

The potency of compounds in inducing activation of immune cells can be assessed using an assay such as the following:

Human peripheral blood mononuclear cells (PBMCs) were purified from healthy donors with Ficoll-Hypaque density centrifugation. Cells were cultured in RPMI-1640 medium (Invitrogen) supplemented with 10% fetal bovine serum, 100 µg/mL ampicillin, 100 µg/mL streptomycin and IL-2 (100 U/mL) for 72 hours in 37° C., 5% $CO_2$. Cells were stimulated with increasing concentrations of GnRH II or GnRH I analogues and analysed for expression of cell specific surface activation markers CD25, CD69 and MHC class I with monoclonal antibodies from BD Pharmingen using flow cytometry.

Solubility and Stability Data (Examples 2 and 3)

Each compound (0.2 mg) is added to PBS (pH 7.4, 0.2 mg/ml) and sonicated for 10 mins then shaken for 20 mins. A T=0 h sample (80 µl) was taken for LC/MS analysis. The solutions were then incubated (37° C. with agitation) in a Techne Roller-Blot Hybridiser HB-3D. Further samples were taken at T=4, 24, 96 h for LC/MS analysis.

LC/MS analysis was conducted on an Agilent HP1100 HPLC system fitted with a diode array detector (DAD), Waters ZQ single quadrupole MS and a Waters X select CSH C18, 2.1 mm×50 mm, 3.5 µm column. LC/MS data was collected for compound identity. LC/UV area under curve (AUC) data was collected for each compound at 280 nm at each of the four timepoints (T=0, 4, 24, 96 h). The trend in this data was interpreted to give each compound a solubility rating of 1 (good) to 5 (poor) and a stability rating (T½).

Calcium Assay in CHO-K1 Cells (Genscript)

Test article sample solutions were dissolved in HBSS buffer (with 20 mM HEPES buffer, pH 7.4) to form the 5× working solution. FLIPR® Calcium 4 assay kit from Molecular devices (R8141) was used as required. In brief, CHO-K1 cells expressing GnRHR (CHO-K1/GnRHR/Ga15, Genscript accession NM_000406) were respectively cultured in the 10-cm dishes and maintained at 37° C./5% CO2. CHO-K1 cells expressing GNRHR were respectively seeded in a 384-well black-wall, clear-bottom plate at a density of 15,000 cells per well in 20 µl of growth medium about 18 hours prior to the day of experiment and maintained at 37° C./5% CO2. Then, 20 µl of dye loading solution was added into the wells and the plates were subsequently placed into a 37° C. incubator for 60 minutes, followed by a 15 minutes' incubation at room temperature. At last, 10 µl of compounds or control agonist were added into respective wells of the assay plate during reading in FLIPR. The plate containing 5× compound and control agonist solution was placed in FLIPR. Solutions were added into the cell plate automatically at the 20 seconds and the fluorescence signal was monitored for an additional 100 seconds (21 sec to 120 sec.). Data were recorded by ScreenWorks (version 3.1) as FMD files with FLIPR and stored on the GenScript computer network for off-line analysis. Data acquisition and analyses was performed using ScreenWorks (version 3.1) program and exported to Excel. The average value of the first 20 seconds' reading was calculated as the baseline and the relative fluorescent units (ΔRFU) intensity values were calculated by subtracting the average value of baseline from the maximum fluorescent units (21 s to 120 s).

The % Stimulation was calculated with the following equation:

% Stimulation=(ΔRFUCompound−ΔRFUBackground)/(ΔRFUAgonist control−ΔRFUBackground)×100

Dose response curves were fitted with four-parameter-logistic-equation by the software GraphPad Prism 6.

Equation: four parameter logistic equation.

$$Y = \text{Bottom} + (\text{Top}-\text{Bottom})/(1+10\hat{}((\text{Log } EC50-X) \times \text{Hillslope}))$$

X is the logarithm of concentration. Y is the response.

Materials

Unless otherwise indicated, all reagents used in the examples below are obtained from commercial sources.

General Synthesis Method

Method A

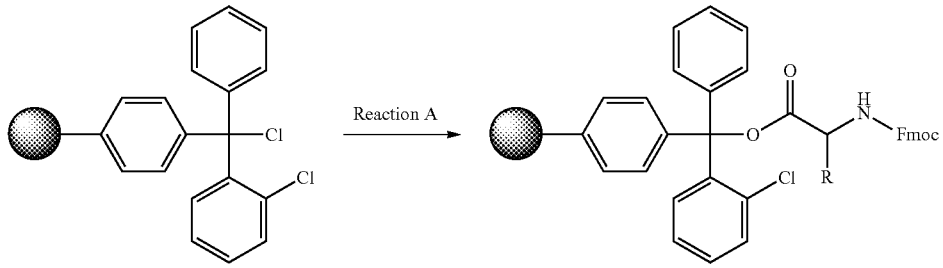

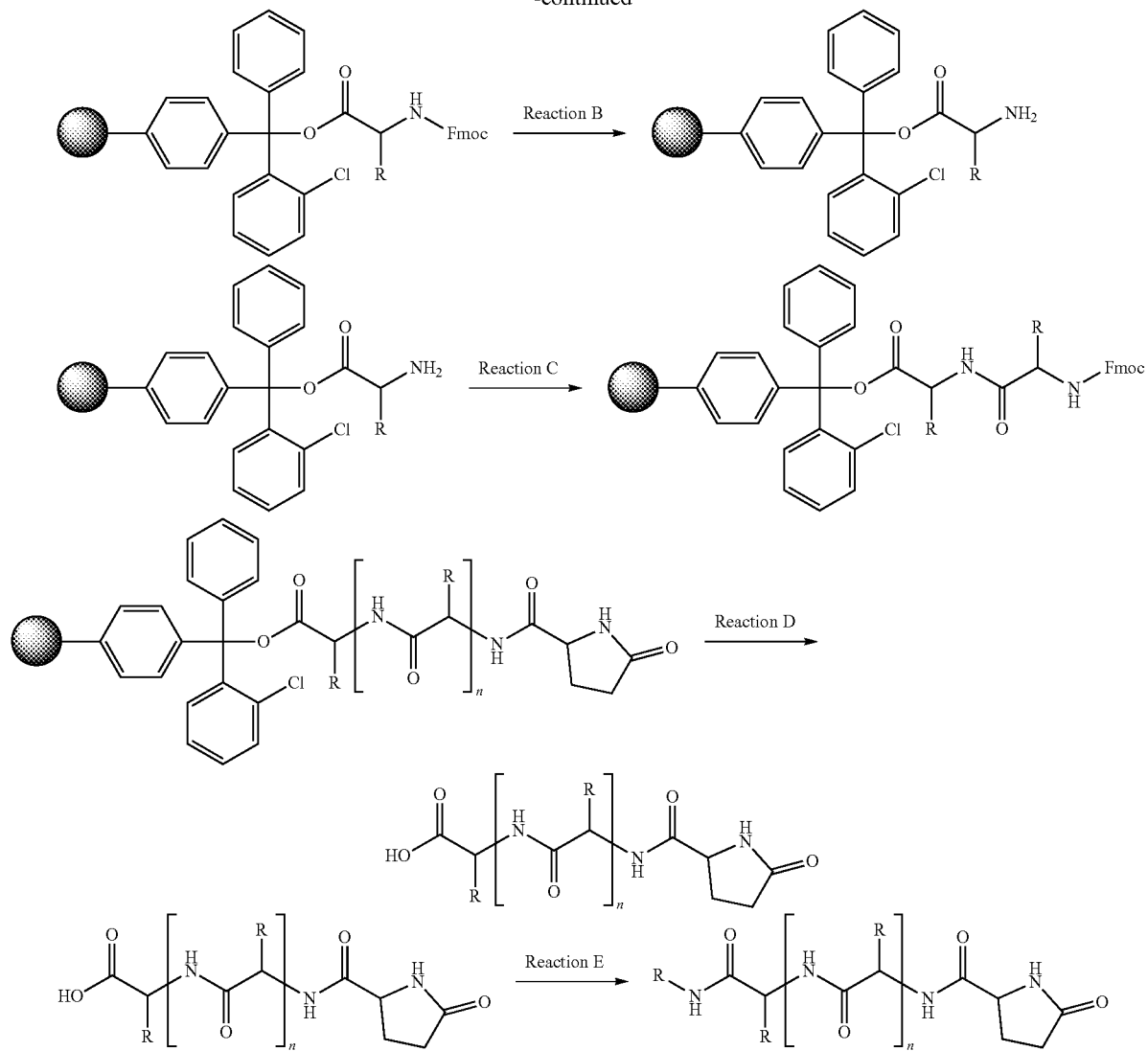

Peptides were prepared using standard Fmoc solid-phase synthesis as per the diagram above. Protected amino acids (Fmoc and tBu or Trt if necessary) were used, and synthesis was performed on 2-chlorotrityl polystyrene resin. Reactions are carried out in the order A, B, C followed by multiple iterations of B and C to build up the desired peptide. When the final amino acid (pyroglutamate—note, reaction C is used to do this, though the amino acid is not Fmoc protected) have been added the final two reactions—D and E—take place in that order to generate a compound of the invention.

Reaction A:

The resin was suspended in dichloromethane (10-20 volume equivalents compared to the resin) and stirred at room temperature. Fmoc protected amino acid (2 equivalents) was added to 1 equivalent of resin in the presence of of diisopropylethylamine (6 equivalents). The reaction was stirred for 0.5 to 1 hour at room temperature. The resin was collected by filtration and washed 6 times with DMF and then used directly in the next step.

Reaction B:

The Fmoc protecting group was removed by the treatment of piperidine (20%) in dimethylformamide (5-10 volume equivalents compared to the resin) at room temperature. The reaction was stirred for up to 1 hour and the resin collected b filtration and then the resin was washed 6 times with DMF and used directly in the next step.

Reaction C:

Fmoc-protected amino acid (4 equivalents) was dissolved in DMF and DIPEA (2 equivalents) added. After stirring at room temperature for one minute these were added to the resin supported amino acid (1 equivalent) from Reaction B was treated with HBTU (1 equivalent) added. The reaction was stirred for up to one hour and before the resin was collected by filtration and washed 6 times with DMF and used directly in the next step. The next step was either reaction B or reaction D depending on the target sequence.

Reaction D:

The protected peptide was cleaved from the resin by treatment with 3-5% trifluoroacetic acid in dichloromethane. The resin was removed by filtration and the peptide accrued by precipitation with ice cold diethyl ether and collection by centrifugation. The solid was washed in further diethyl ether and then dried under vacuum before being used in the next step.

Reaction E:

The C-terminal amide was formed by dissolving the peptide from Reaction D (1 equivalent) in DMF, monoalkylamine (20-50 equivalents) and HBTU (2-3 equivalents) were added and the reaction stirred at room temperature for up to 3 hours. The reaction was diluted with water and the crude peptide was then purified as detailed below.

Method B

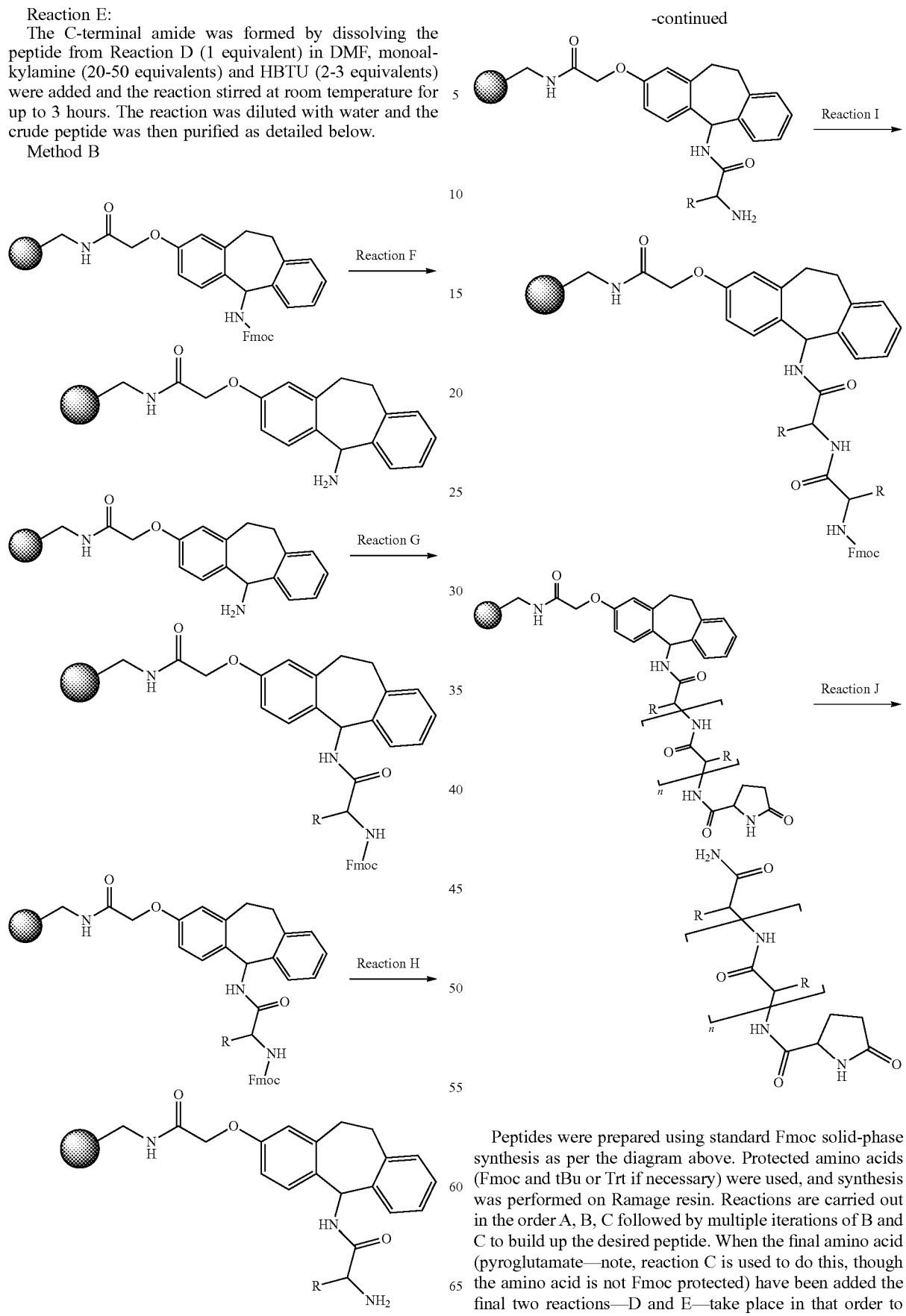

Peptides were prepared using standard Fmoc solid-phase synthesis as per the diagram above. Protected amino acids (Fmoc and tBu or Trt if necessary) were used, and synthesis was performed on Ramage resin. Reactions are carried out in the order A, B, C followed by multiple iterations of B and C to build up the desired peptide. When the final amino acid (pyroglutamate—note, reaction C is used to do this, though the amino acid is not Fmoc protected) have been added the final two reactions—D and E—take place in that order to generate a compound of the invention.

Reaction F:

Fmoc Ramage resin is suspended in DMF (5-10 volume equivalents compared to resin) containing 20% piperidine. The reaction was stirred for up to 1 hour at room temperature and the resin collected by filtration and washed 6 times with DMF and used directly in the next reaction.

Reaction G:

Fmoc-protected amino acid (5 equivalents) was dissolved in DMF and DIPEA (2 equivalents) added. After stirring at room temperature for one minute these were added to the resin supported amino acid (1 equivalent) from Reaction F was treated with HBTU (1 equivalent) added. The reaction was stirred for up to one hour and before the resin was collected by filtration and washed 6 times with DMF and used directly in the next step.

Reaction H:

The Fmoc protecting group was removed by the treatment of piperidine (20%) in dimethylformamide (5-10 volume equivalents compared to the resin) at room temperature. The reaction was stirred for up to 1 hour and the resin collected b filtration and then the resin was washed 6 times with DMF and used directly in the next step.

Reaction I:

Fmoc-protected amino acid (4 equivalents) was dissolved in DMF and DIPEA (2 equivalents) added. After stirring at room temperature for one minute these were added to the resin supported amino acid (1 equivalent) from Reaction H was treated with HBTU (1 equivalent) added. The reaction was stirred for up to one hour and before the resin was collected by filtration and washed 6 times with DMF and used directly in the next step. The next step was either reaction H or reaction J depending on the target sequence.

Reaction J:

The peptide was cleaved from the resin by treatment with 90% trifluoroacetic acid with 2.5% water, 2.5% triisopropylsilane and 5% dichloromethane. The resin was removed by filtration and the peptide accrued by precipitation with ice cold diethyl ether and collection by centrifugation. The crude peptide was then purified as detailed below.

Purification

The crude peptides were individually dissolved in acetonitrile/H$_2$O (1:1, v/v) and purified by preparative HPLC with a C18 column using a water (0.1% TFA)-acetonitrile (0.1% TFA) gradient. The final purity of the peptides was confirmed by analytical HPLC. Peptide was lyophilized before storage at −20° C.

Compound Analysis—Identity and Purity

Analysis Method A

For analysis, the compounds were dissolved in methanol:water (9:1, 0.1 mg/ml) and a 150 µl portion was placed in an HPLC microvial and centrifuged at 14000 rpm for 3 minutes. The sample was then examined by high performance liquid chromatography with diode array (HPLC-DAD) and mass spectrometry (HPLC-MS) detection. HPLC-DAD-MS was performed using an Agilent 1100 HPLC system comprising of quaternary pump, auto sampler, column oven and diode array detector coupled to a Waters ZQ single quadrupole mass spectrometer. The same reverse-phase Waters Xselect CSH C18, 2.1 mm×50 mm, 3.5 µm particle size column was used for all compounds and was fitted with a Waters VanGuard CSH C18, 2.1 mm×5 mm, 3.5 µm particle size guard column and Waters Acquity, 0.2 µm in-line column filter. The column was used at a flow rate of 1 ml/min maintained at a temperature of 60° C. The solvents used were 0.17% formic acid in 95% acetonitrile, 5% water (solvent B) and 10 mM ammonium formate, 0.2% formic acid in water (solvent A), with a gradient as follows: 5% solvent B from 0 to 0.2 min, 5 to 50% solvent B from 0.2 to 9.3 min, 50 to 95% solvent B from 9.3 to 9.5 min, 95% solvent B from 9.5 to 11 min, 95 to 5% solvent B from 11 to 11.05 min and re-equilibration with 5% solvent B from 11.05 to 11.5 min. Nitrogen was used as auxiliary and sheath gas. Source voltage was set at 3400 V, cone voltage set at 31 V with a gas flow of 50 L/hour, drying gas flow rate at 550 L/hour and drying gas temperature at 350° C.

Compound Analysis—Solubility and Stability in Solution

Analysis Method B

For solubility and stability analysis, the compounds were dissolved (0.2 mg/ml) in phosphate buffer solution (PBS, 10 mM, pH 7.4) and shaken at room temperature for 20 minutes. A T=0 hour sample was taken (80 µl) and centrifuged at 14000 rpm for 3 minutes then analysed by Analysis method A as above. The bulk samples were placed in a Techne Roller-Blot HB-3D Rolling Hybridiser at 37° C. and only removed when a sample (80 µl) was taken at time points T=4, 24 and 96 hours. The samples were centrifuged at 14000 rpm for 3 mins then analysed by HPLC-DAD-MS as above. The UV area under curve at 280 nm was recorded at each time point.

EXAMPLES

Example 1—Compound Synthesis

Compounds of the invention were made according to the methods set out in the General Synthesis Method.

| Compound no. | R1 | R2 | R3 | R4 | R5 | Synthesis Method |
|---|---|---|---|---|---|---|
| 6 | imidazole | OtBu | isopropyl | guanidinyl (H$_2$N-C(=NH)-NH-CH$_2$-) | Et | A |

-continued

| Compound no. | R1 | R2 | R3 | R4 | R5 | Synthesis Method |
|---|---|---|---|---|---|---|
| 8 | 4-hydroxybenzyl | tBuO-CH2- | indol-3-ylmethyl | 3-guanidinopropyl | Et | A |
| 9 | 4-hydroxybenzyl | tBuO-CH2- | isobutyl | 4-hydroxybenzyl | Et | A |
| 10 | imidazol-4-ylmethyl | tBuO-CH2- | indol-3-ylmethyl | 3-guanidinopropyl | Et | A |
| 11 | imidazol-4-ylmethyl | tBuO-CH2- | isobutyl | 4-hydroxybenzyl | Et | A |
| 12 | 4-hydroxybenzyl | tBuO-CH2- | indol-3-ylmethyl | 4-hydroxybenzyl | Et | A |
| 13 | imidazol-4-ylmethyl | tBuO-CH2- | indol-3-ylmethyl | 4-hydroxybenzyl | Et | A |
| 14 | 4-hydroxybenzyl | indol-3-ylmethyl | isobutyl | 4-hydroxybenzyl | CH2CONH2 | B |

-continued

| Compound no. | R1 | R2 | R3 | R4 | R5 | Synthesis Method |
|---|---|---|---|---|---|---|
| 16 | 4-imidazolyl-CH2- | indol-3-yl-CH2- | isobutyl | 4-hydroxybenzyl | CH2CONH2 | B |
| 20 | 4-imidazolyl-CH2- | indol-3-yl-CH2- | indol-3-yl-CH2- | 3-guanidinopropyl | CH2CONH2 | B |
| 23 | 4-imidazolyl-CH2- | naphth-2-yl-CH2- | isobutyl | 3-guanidinopropyl | CH2CONH2 | B |
| 24 | 4-hydroxybenzyl | naphth-2-yl-CH2- | indol-3-yl-CH2- | 3-guanidinopropyl | CH2CONH2 | B |
| 25 | 4-hydroxybenzyl | naphth-2-yl-CH2- | isobutyl | 4-hydroxybenzyl | CH2CONH2 | B |
| 27 | 4-imidazolyl-CH2- | naphth-2-yl-CH2- | indol-3-yl-CH2- | 3-guanidinopropyl | CH2CONH2 | B |

-continued

| Compound no. | R1 | R2 | R3 | R4 | R5 | Synthesis Method |
|---|---|---|---|---|---|---|
| 28 | 4-imidazolyl-CH₂- | 2-naphthyl-CH₂- | isobutyl | 4-hydroxybenzyl | CH₂CONH₂ | B |
| 30 | 4-hydroxybenzyl | 2-naphthyl-CH₂- | 3-indolyl-CH₂- | 4-hydroxybenzyl | CH₂CONH₂ | B |
| 33 | 4-imidazolyl-CH₂- | 2-naphthyl-CH₂- | 3-indolyl-CH₂- | 4-hydroxybenzyl | CH₂CONH₂ | B |
| 42 | 4-imidazolyl-CH₂- | tBuO-CH₂- | isobutyl | guanidinopropyl | Et | A |
| 44 | 4-hydroxybenzyl | tBuO-CH₂- | 3-indolyl-CH₂- | guanidinopropyl | Et | A |
| 45 | 4-hydroxybenzyl | isobutyl | isobutyl | 4-hydroxybenzyl | Et | A |
| 47 | 4-imidazolyl-CH₂- | isobutyl | 3-indolyl-CH₂- | guanidinopropyl | Et | A |

-continued

| Compound no. | R1 | R2 | R3 | R4 | R5 | Synthesis Method |
|---|---|---|---|---|---|---|
| 48 | 4-imidazolyl-CH2- | isobutyl | isobutyl | 4-hydroxybenzyl | Et | A |
| 49 | 4-hydroxybenzyl | isobutyl | indol-3-yl-CH2- | 4-hydroxybenzyl | Et | A |
| 50 | 4-imidazolyl-CH2- | isobutyl | indol-3-yl-CH2- | 4-hydroxybenzyl | Et | A |
| 56 | 4-imidazolyl-CH2- | 1-benzylimidazol-4-yl-CH2- | isobutyl | guanidinopropyl | Et | A |
| 59 | 4-hydroxybenzyl | 1-benzylimidazol-4-yl-CH2- | isobutyl | 4-hydroxybenzyl | Et | A |
| 60 | 4-imidazolyl-CH2- | 1-benzylimidazol-4-yl-CH2- | indol-3-yl-CH2- | guanidinopropyl | Et | A |

-continued

| Compound no. | R1 | R2 | R3 | R4 | R5 | Synthesis Method |
|---|---|---|---|---|---|---|
| 61 | 1H-imidazol-4-ylmethyl | 1-benzyl-1H-imidazol-4-ylmethyl | isobutyl | 4-hydroxybenzyl | Et | A |
| 62 | 4-hydroxybenzyl | 1-benzyl-1H-imidazol-4-ylmethyl | 1H-indol-3-ylmethyl | 4-hydroxybenzyl | Et | A |
| 63 | 1H-imidazol-4-ylmethyl | 1-benzyl-1H-imidazol-4-ylmethyl | 1H-indol-3-ylmethyl | 4-hydroxybenzyl | Et | A |
| 64 | 4-hydroxybenzyl | 1H-indol-3-ylmethyl | 1H-indol-3-ylmethyl | 4-hydroxybenzyl | $CH_2CONH_2$ | |
| 65 | 1H-imidazol-4-ylmethyl | 1H-indol-3-ylmethyl | 1H-indol-3-ylmethyl | 4-hydroxybenzyl | $CH_2CONH_2$ | |

-continued

| Compound no. | R1 | R2 | R3 | R4 | R5 | Synthesis Method |
|---|---|---|---|---|---|---|
| 66 | 4-hydroxybenzyl | indol-3-ylmethyl | indol-3-ylmethyl | 4-guanidinobutyl | CH$_2$CONH$_2$ | |
| 67 | 4-hydroxybenzyl | (1-benzylimidazol-4-yl)methyl | indol-3-ylmethyl | 4-guanidinobutyl | Et | |
| 68 | (imidazol-4-yl)methyl | indol-3-ylmethyl | isobutyl | 4-guanidinobutyl | CH$_2$CONH$_2$ | |

| Compound number | Salt form | Retention Time (Analysis method A) | m/z (Analysis method A) |
|---|---|---|---|
| 6 | TFA | 4.15 | 1213.8 |
| 8 | TFA | 5.5 | 1312.7 |
| 9 | TFA | 6.64 | 1246.8 |
| 10 | TFA | 4.27 | 1286.9 |
| 11 | TFA | 5.35 | 1220.9 |
| 12 | TFA | 6.75 | 1319.7 |
| 13 | TFA | 5.53 | 1293.7 |
| 14 | TFA | 6.13 | 1318.7 |
| 16 | TFA | 4.93 | 1292.8 |
| 20 | TFA | 4.02 | 1358.9 |
| 23 | TFA | 4.79 | 1296.7 |
| 24 | TFA | 5.84 | 1395.7 |
| 25 | TFA | 7.19 | 1329.6 |
| 27 | TFA | 4.91 | 1369.6 |
| 28 | TFA | 5.92 | 1303.8 |
| 30 | TFA | 7.20 | 1402.7 |
| 33 | TFA | 6.00 | 1376.4 |
| 42 | TFA | 3.90 | 1183.8 |
| 44 | TFA | 5.23 | 1282.8 |
| 45 | TFA | 6.35 | 1216.8 |
| 47 | TFA | 4.00 | 1256.8 |
| 48 | TFA | 5.12 | 1190.8 |
| 49 | TFA | 6.56 | 1290.0 |
| 50 | TFA | 5.30 | 1263.7 |
| 56 | TFA | 3.42 | 1297.7 |
| 59 | TFA | 5.22 | 1330.8 |
| 60 | TFA | 3.81 | 1370.6 |
| 61 | TFA | 4.36 | 1304.7 |
| 62 | TFA | 5.60 | 1403.5 |
| 63 | TFA | 4.69 | 1377.7 |
| 64 | TFA | 6.19 | 1391.7 |
| 65 | TFA | 5.09 | 1366.0 |
| 66 | TFA | 4.92 | 1384.7 |
| 67 | TFA | 4.47 | 1396.9 |
| 68 | TFA | 3.83 | 1285.8 |

Example 2—Solubility Analysis

The solubility of compounds of the invention was tested as described in the general methods. Solubility was then graded according to a rating between 1 to 5, where 1 is most soluble and 5 is least soluble.

| Compound number | Solubility grading |
|---|---|
| Buserelin acetate | 1 |
| Triptorelin acetate | 2 |
| Naferelin acetate | 2 |
| Histrelin acetate | 4 |
| Leuprorelin acetate | 2 |
| Buserelin TFA | 2 |
| Triptorelin TFA | 2 |
| Naferelin TFA | 1 |
| Histrelin TFA | 2 |
| Leuprorelin TFA | 1 |
| 6 | 1 |

| Compound number | Solubility grading |
|---|---|
| 8 | 2 |
| 9 | 1 |
| 10 | 1 |
| 11 | 1 |
| 12 | 4 |
| 13 | 3 |
| 14 | 4 |
| 16 | 2 |
| 20 | 3 |
| 23 | 1 |
| 24 | 5 |
| 25 | 4 |
| 33 | 2 |
| 30 | 1 |
| 28 | 2 |
| 27 | 1 |
| 56 | 1 |
| 67 | 1 |
| 59 | 4 |
| 63 | 5 |
| 62 | 5 |
| 61 | 3 |
| 60 | 2 |
| 42 | 1 |
| 44 | 2 |
| 45 | 2 |
| 50 | 1 |
| 49 | 4 |
| 48 | 2 |
| 47 | 1 |
| 68 | 1 |
| 66 | 5 |
| 14 | 4 |
| 65 | 4 |
| 64 | 5 |
| 16 | 2 |
| 20 | 3 |

Example 3—Stability Analysis

The stability of compounds of the invention in aqueous media (PBS ph7.4) was tested as described in the general methods. Stability was then graded according to a rating where t1/2>96 minutes was shown as + and stability less than this was shown as −.

| Compound number | Stability grading |
|---|---|
| 6 | + |
| 8 | + |
| 9 | + |
| 10 | + |
| 11 | + |
| 12 | + |
| 13 | + |
| 14 | + |
| 16 | + |
| 20 | + |
| 23 | + |
| 24 | − |
| 25 | − |
| 33 | − |
| 30 | − |
| 28 | + |
| 27 | + |
| 56 | + |
| 67 | − |
| 59 | − |
| 63 | − |
| 62 | − |
| 61 | + |
| 60 | + |
| 42 | + |
| 44 | + |
| 45 | + |
| 50 | + |
| 49 | + |
| 48 | + |
| 47 | + |
| 68 | + |
| 66 | + |
| 14 | + |
| 65 | + |
| 64 | − |
| 16 | + |
| 20 | + |

Example 4—GnRH R Stimulation

The ability of compounds of the invention to stimulate GnRHR was assessed by using a calcium assay with CHO-K1 cells (Genscript), see the general methods for details. Activity was then recorded as percentage stimulation at 1 µM.

| Compound number | GNRHR Stimulation at 1 µM |
|---|---|
| Buserelin | 94 |
| Leuprorelin | 107 (n = 2) |
| Goserelin | 99 |
| Gonadorelin | 102 |
| Nafarelin | 100 (n = 2) |
| 6 | 88 |
| 8 | 86 |
| 9 | 78 |
| 10 | 81 |
| 11 | 76 |
| 12 | 80 |
| 13 | 87 |
| 14 | 78 |
| 16 | 76 |
| 20 | 75 |
| 23 | 106 |
| 24 | 87 |
| 25 | 82 |
| 33 | 67 |
| 30 | 12 |
| 28 | 95 |
| 27 | 108 |
| 56 | 96 |
| 67 | 117 |
| 59 | 85 |
| 63 | 77 |
| 62 | 77 |
| 61 | 112 |
| 60 | 102 |
| 42 | 102 |
| 44 | 111 |
| 45 | 105 |
| 50 | 105 |
| 49 | 77 |
| 48 | 118 |
| 47 | 119 |
| 68 | 86 |
| 66 | 83 |
| 14 | 78 |
| 65 | 72 |
| 64 | 50 |
| 16 | 76 |
| 20 | 75 |

REFERENCES

1. Gonadotropin secretion and its control. Fink G, The physiology of reproduction 1998.

2. Immunomodulatory actions of gonadal steroids may be mediated by gonadotropin-releasing hormone. Jacobson J D and Ansari M A, Endocrinology 2004; 145(1):330-6.
3. Unusual morphologic features of uterine leiomyomas treated with gonadotropin-releasing hormone agonists: massive lymphoid infiltration and vasculitis. McClean G and McCluggage W G, Int J Surg Pathol. 2003; 11(4): 339-44.
4. Massive lymphocytic infiltration of uterine leyomyomas associated with GnRH agonist treatment. Bardsley V et al., Histopathology 1998; 33(1):80-2.
5. Chronic plasma cell endometritis in hysterectomy specimens of HIV-infected women: a retrospective analysis. Kerr-Layton J A et al., Infect Dis Obstet Gynecol. 1998; 6(4):186-90
6. Serum dihydrotestosterone and testosterone concentrations in human immunodeficiency virus-infected men with and without weight loss. Arver S et al., J Androl 1999; 20(5):611-8.
7. Prevalence of endocrine dysfunction in HIV-infected men. Brockmeyer G et al., Horm Res 2000; 54(5-6):294-5.
8. Gonadotropin-releasing hormone increases CD4-T-lymphocyte numbers in an animal model of immunodeficiency. Jacobson J D et al., J Allergy Clin Immunol. 1999; 104:653-8.
9. Second gene for gonadotropin-releasing hormone in humans. White et al., PNAS 1998; Jan. 6; 95(1):305-9.

10. A transcriptionally active human type II gonadotropin-releasing hormone receptor gene homolog overlaps two genes in the antisense orientation on chromosome 1q.12. Morgan et al., Endocrinology. 2003 February; 144(2): 423-36
11. Gonadotropin-releasing hormone (GnRH)-binding sites in human breast cancer cell lines and inhibitory effects of GnRH antagonists. Eidne et al., J Clin Endocrinol Metab. 1987 Mar.; 64(3):425-32

All references referred to in this application, including patent and patent applications, are incorporated herein by reference to the fullest extent possible.

The invention claimed is:

1. A method of treating a GnRH receptor-expressing cancer in a subject in need thereof by stimulating the immune system of the subject, comprising administering to the subject an effective amount of a compound of formula (I):

105

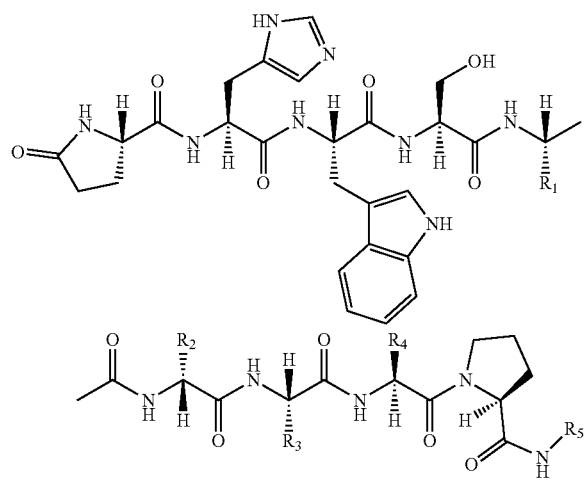

(I)

or a pharmaceutically acceptable salt thereof, wherein

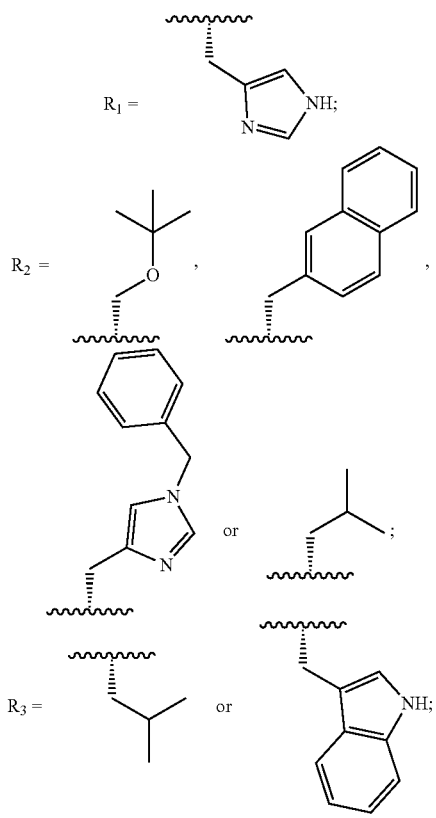

106

-continued

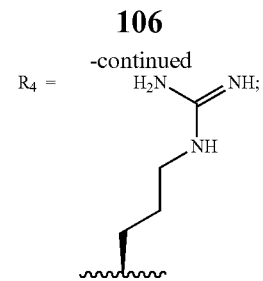

$R_5$=Me, Et, $CH_2CF_3$, iPr, nPr, nBu, iBu, sBu, tBu, cyclo-propyl $CH_2CONH_2$, or $NHCONH_2$; and wherein the GnRH receptor-expressing cancer is selected from Adrenal Cancer, Anal Cancer, Bile Duct Cancer, Bladder Cancer, Bone Cancer, Brain/CNS Tumors, Castleman Disease, Colon/Rectum Cancer, Esophagus Cancer, Eye Cancer, Gallbladder Cancer, Gastrointestinal Carcinoid Tumors, Gastrointestinal Stromal Tumor (GIST), Hodgkin Disease, Kaposi Sarcoma, Kidney Cancer, Laryngeal and Hypopharyngeal Cancer, Acute Myeloid Leukemia, Chronic Lymphocytic Leukemia, Acute Lymphocytic Leukemia, Chronic Myeloid Leukemia, Chronic Myelomonocytic Leukemia, Liver Cancer, Lymphoma, Malignant Mesothelioma, Multiple Myeloma, Myelodysplastic Syndrome, Nasal Cavity and Paranasal Sinus Cancer, Nasopharyngeal Cancer, Neuroblastoma, Non-Hodgkin Lymphoma, Oral Cavity and Oropharyngeal Cancer, Osteosarcoma, Penile Cancer, Retinoblastoma, Rhabdomyosarcoma, Salivary Gland Cancer, Basal and Squamous Cell Skin Cancer, Merkel Cell Skin Cancer, Small Intestine Cancer, Stomach Cancer, Thymus Cancer, Uterine Sarcoma, Vulvar Cancer, Waldenstrom Macroglobulinemia, and Wilms Tumor.

2. The method according to claim 1, wherein $R_5$=Et or $CH_2CONH_2$.

3. The method according to claim 1, wherein $R_5$=Me, iPr, nPr, nBu, iBu, sBu, or tBu.

4. The method according to claim 1, wherein:

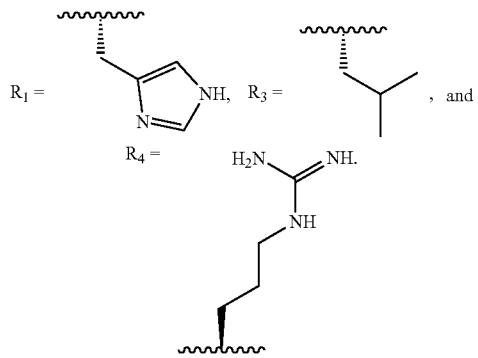

5. The method according to claim 4, wherein the compound according to formula (I) is one of the following compounds:

| Compound | $R_1$ | $R_2$ | $R_3$ | $R_4$ | $R_5$ |
|---|---|---|---|---|---|
| 1 | imidazolylmethyl | tBuO-CH2 | iBu | guanidinopropyl | $C_2CONH_2$ |

-continued

| Compound | R₁ | R₂ | R₃ | R₄ | R₅ |
|---|---|---|---|---|---|
| 6 | 4-imidazolylmethyl | tert-butoxymethyl | isobutyl | 3-guanidinopropyl | Et |
| 23 | 4-imidazolylmethyl | 2-naphthylmethyl | isobutyl | 3-guanidinopropyl | C₂CONH₂ |
| 29 | 4-imidazolylmethyl | 2-naphthylmethyl | isobutyl | 3-guanidinopropyl | Et |
| 37 | 4-imidazolylmethyl | isobutyl | isobutyl | 3-guanidinopropyl | C₂CONH₂ |
| 42 | 4-imidazolylmethyl | isobutyl | isobutyl | 3-guanidinopropyl | Et |
| 51 | 4-imidazolylmethyl | (1-benzylimidazol-4-yl)methyl | isobutyl | 3-guanidinopropyl | C₂CONH₂ | or

-continued

| Compound | R₁ | R₂ | R₃ | R₄ | R₅ |
|---|---|---|---|---|---|
| 56 | imidazolylmethyl | N-benzyl imidazolylmethyl | isobutyl | guanidinobutyl | Et | or a pharmaceutically acceptable salt of any of these.

6. The method according to claim 1, wherein:

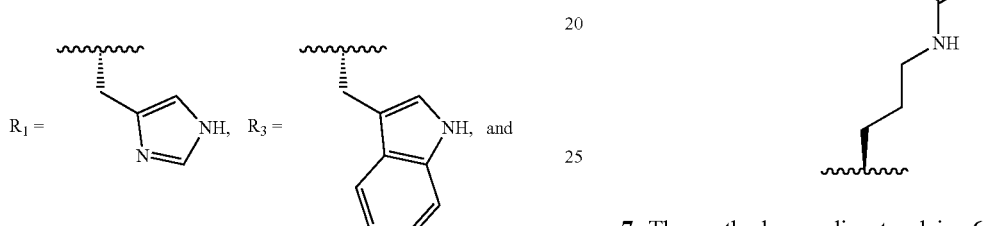

7. The method according to claim 6, wherein the compound of formula (I) is one of the following compounds:

| Compound | R₁ | R₂ | R₃ | R₄ | R₅ |
|---|---|---|---|---|---|
| 4 | imidazolylmethyl | tert-butoxymethyl | indolylmethyl | guanidinobutyl | $C_2CONH_2$ |
| 10 | imidazolylmethyl | tert-butoxymethyl | indolylmethyl | guanidinobutyl | Et |
| 27 | imidazolylmethyl | naphthylmethyl | indolylmethyl | guanidinobutyl | $C_2CONH_2$ |
| 34 | imidazolylmethyl | naphthylmethyl | indolylmethyl | guanidinobutyl | Et |

| Compound | R₁ | R₂ | R₃ | R₄ | R₅ |
|---|---|---|---|---|---|
| 40 | imidazole-CH₂- | isobutyl | indole-CH₂- | H₂N-C(=NH)-NH-(CH₂)₃- | C₂CONH₂ |
| 47 | imidazole-CH₂- | isobutyl | indole-CH₂- | H₂N-C(=NH)-NH-(CH₂)₃- | Et |
| 54 | imidazole-CH₂- | N-benzyl-imidazole-CH₂- | indole-CH₂- | H₂N-C(=NH)-NH-(CH₂)₃- | C₂CONH₂ | or

| 60 | imidazole-CH₂- | N-benzyl-imidazole-CH₂- | indole-CH₂- | H₂N-C(=NH)-NH-(CH₂)₃- | Et | or a pharmaceutically acceptable salt of any of these.

8. The method according to claim 1, wherein

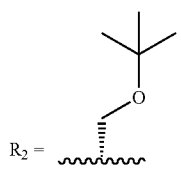

$R_2 = $

9. The method according to claim 8, wherein the compound of formula (I) is one of the following compounds:

| Compound | R₁ | R₂ | R₃ | R₄ | R₅ |
|---|---|---|---|---|---|
| 1 | histidine side chain | O-tBu (Ser(tBu)) | isobutyl (Leu) | arginine side chain | C₂CONH₂ |
| 4 | histidine side chain | O-tBu (Ser(tBu)) | indole-CH₂ (Trp) | arginine side chain | C₂CONH₂ |
| 6 | histidine side chain | O-tBu (Ser(tBu)) | isobutyl (Leu) | arginine side chain | Et |
| 10 | histidine side chain | O-tBu (Ser(tBu)) | indole-CH₂ (Trp) | arginine side chain | Et | or a pharmaceutically acceptable salt of any of these.

10. A method of treating a GnRH receptor-expressing cancer in a subject in need thereof by stimulating the immune system of the subject, comprising administering to the subject an effective amount of a pharmaceutical composition comprising:

a compound of formula (I):

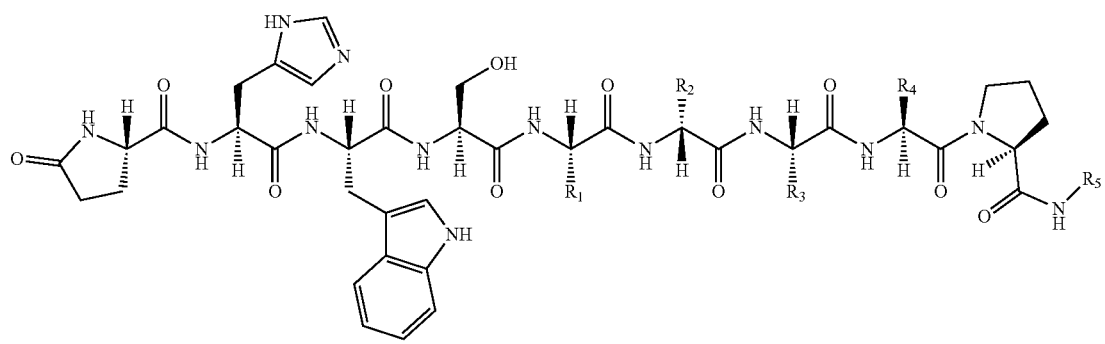

(I)

or a pharmaceutically acceptable salt thereof, wherein

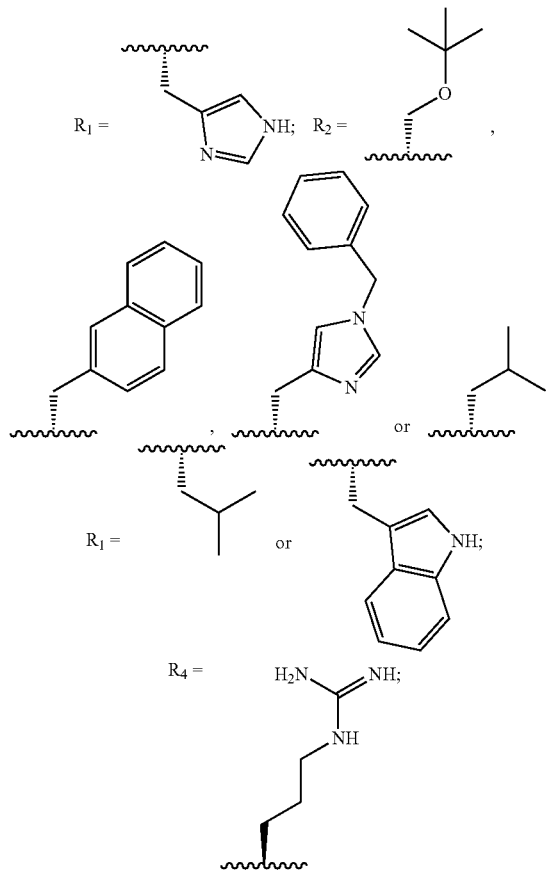

R5=Me, Et, CH$_2$CF$_3$, iPr, nPr, nBu, iBu, sBu, tBu, cyclopropyl CH$_2$CONH$_2$, or NHCONH$_2$; and one or more pharmaceutically acceptable excipients.

11. A method of treating a GnRH receptor-expressing cancer in a subject in need thereof by stimulating the immune system of the subject, comprising administering to the subject an effective amount of a compound selected from one of the following numbered compounds:

1: pGlu-His-Trp-Ser-His-D-Ser(tBu)-Leu-Arg-Pro-Gly-NH$_2$,
6: pGlu-His-Trp-Ser-His-D-Ser(tBu)-Leu-Arg-Pro-NHEt,
23: pGlu-His-Trp-Ser-His-D-Nal-Leu-Arg-Pro-Gly-NH$_2$,
29: pGlu-His-Trp-Ser-His-D-Nal-Leu-Arg-Pro-NHEt,
37: pGlu-His-Trp-Ser-His-D-Leu-Leu-Arg-Pro-Gly-NH$_2$,
42: pGlu-His-Trp-Ser-His-D-Leu-Leu-Arg-Pro-NHEt,
51: pGlu-His-Trp-Ser-His-D-Bhi-Leu-Arg-Pro-Gly-NH$_2$,
56: pGlu-His-Trp-Ser-His-D-Bhi-Leu-Arg-Pro-NHEt,
4: pGlu-His-Trp-Ser-His-D-Ser(tBu)-Trp-Arg-Pro-Gly-amide,
10: pGlu-His-Trp-Ser-His-D-Ser(tBu)-Trp-Arg-Pro-NHEt,
27: pGlu-His-Trp-Ser-His-D-Nal-Trp-Arg-Pro-Gly-amide,
34: pGlu-His-Trp-Ser-His-D-Nal-Trp-Arg-Pro-NHEt,
40: pGlu-His-Trp-Ser-His-D-Leu-Trp-Arg-Pro-Gly-amide,
47: pGlu-His-Trp-Ser-His-D-Leu-Trp-Arg-Pro-NHEt,
54: pGlu-His-Trp-Ser-His-D-Bhi-Trp-Arg-Pro-Gly-amide, and
60: pGlu-His-Trp-Ser-His-D-Bhi-Trp-Arg-Pro-NHEt;

or a pharmaceutically acceptable salt of any of these.

12. The method according to claim 11, wherein the GnRH receptor-expressing cancer is selected from Adrenal Cancer, Anal Cancer, Bile Duct Cancer, Bladder Cancer, Bone Cancer, Brain/CNS Tumors, Castleman Disease, Colon/Rectum Cancer, Esophagus Cancer, Eye Cancer, Gallbladder Cancer, Gastrointestinal Carcinoid Tumors, Gastrointestinal Stromal Tumor (GIST), Hodgkin Disease, Kaposi Sarcoma, Kidney Cancer, Laryngeal and Hypopharyngeal Cancer, Acute Myeloid Leukemia, Chronic Lymphocytic Leukemia, Acute Lymphocytic Leukemia, Chronic Myeloid Leukemia, Chronic Myelomonocytic Leukemia, Liver Cancer, Lymphoma, Malignant Mesothelioma, Multiple Myeloma, Myelodysplastic Syndrome, Nasal Cavity and Paranasal Sinus Cancer, Nasopharyngeal Cancer, Neuroblastoma, Non-Hodgkin Lymphoma, Oral Cavity and Oropharyngeal Cancer, Osteosarcoma, Penile Cancer, Retinoblastoma, Rhabdomyosarcoma, Salivary Gland Cancer, Basal and Squamous Cell Skin Cancer, Merkel Cell Skin Cancer, Small Intestine Cancer, Stomach Cancer, Thymus Cancer, Uterine Sarcoma, Vulvar Cancer, Waldenstrom Macroglobulinemia, and Wilms Tumor.

* * * * *

UNITED STATES PATENT AND TRADEMARK OFFICE
CERTIFICATE OF CORRECTION

PATENT NO. : 11,434,258 B2
APPLICATION NO. : 16/479507
DATED : September 6, 2022
INVENTOR(S) : Ola Winqvist Page 1 of 1

It is certified that error appears in the above-identified patent and that said Letters Patent is hereby corrected as shown below:

In the Claims

In Column 106, Claim 5, Line 55, delete "$C_2CONH_2$" and insert -- $CH_2CONH_2$ --, therefor.

In Column 108, Claim 5, Line 3, delete "$C_2CONH_2$" and insert -- $CH_2CONH_2$ --, therefor.

In Column 108, Claim 5, Line 5, delete "$C_2CONH_2$" and insert -- $CH_2CONH_2$ --, therefor.

In Column 108, Claim 5, Line 7, delete "$C_2CONH_2$" and insert -- $CH_2CONH_2$ --, therefor.

In Column 110, Claim 7, Line 29, delete "$C_2CONH_2$" and insert -- $CH_2CONH_2$ --, therefor.

In Column 110, Claim 7, Line 31, delete "$C_2CONH_2$" and insert -- $CH_2CONH_2$ --, therefor.

In Column 112, Claim 7, Line 2, delete "$C_2CONH_2$" and insert -- $CH_2CONH_2$ --, therefor.

In Column 112, Claim 7, Line 4, delete "$C_2CONH_2$" and insert -- $CH_2CONH_2$ --, therefor.

In Column 114, Claim 9, Line 2, delete "$C_2CONH_2$" and insert -- $CH_2CONH_2$ --, therefor.

In Column 114, Claim 9, Line 3, delete "$C_2CONH_2$" and insert -- $CH_2CONH_2$ --, therefor.

In Column 115, Claim 10, Line 23, delete "$R_1=$" and insert -- $R_3=$ --, therefor.

In Column 115, Claim 10, Line 38, delete "R5=" and insert -- $R_5=$ --, therefor.

Signed and Sealed this
Twentieth Day of December, 2022

*Katherine Kelly Vidal*

Katherine Kelly Vidal
*Director of the United States Patent and Trademark Office*